(12) United States Patent
Hines et al.

(10) Patent No.: US 10,307,049 B2
(45) Date of Patent: *Jun. 4, 2019

(54) METHODS, DEVICES, SYSTEMS, ASSEMBLIES, AND KITS FOR TISSUE RETRACTION IN AN ORAL CAVITY

(71) Applicant: ULTRADENT PRODUCTS, INC., South Jordan, UT (US)

(72) Inventors: Craig Hines, Lihue, HI (US); Curtis Pontynen, San Jose, CA (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,011

(22) Filed: May 26, 2016

(65) Prior Publication Data

US 2016/0270880 A1 Sep. 22, 2016

Related U.S. Application Data

(63) Continuation of application No. 13/829,609, filed on Mar. 14, 2013, now Pat. No. 9,387,054, which is a
(Continued)

(51) Int. Cl.
*A61B 1/24* (2006.01)
*A61B 1/32* (2006.01)
(Continued)

(52) U.S. Cl.
CPC .............. *A61B 1/24* (2013.01); *A61B 1/0684* (2013.01); *A61B 1/32* (2013.01); *A61B 6/14* (2013.01);
(Continued)

(58) Field of Classification Search
CPC ......... A61C 5/14; A61C 5/122; A61C 9/0033; A61C 17/04; A61C 19/003; A61C 5/90;
(Continued)

(56) References Cited

U.S. PATENT DOCUMENTS 2,589,504 A    3/1952   Miller
2,812,758 A    11/1957   Blumneschein
(Continued)

FOREIGN PATENT DOCUMENTS

CH           695235 A5    2/2006
CH           695235 A8    3/2006
(Continued)

OTHER PUBLICATIONS

Radius of Curavture from https://en.wikipedia.org/wiki/Radius_of_curvature on Jul. 27, 207.*
(Continued)

*Primary Examiner* — Heidi M Eide
(74) *Attorney, Agent, or Firm* — Maschoff Brennan

(57) ABSTRACT

Provided herein is a retraction device for retracting soft tissue from the dental surfaces in the oral cavity of a patient. The retraction device is comprised of a topology conformable structure, where the topology conformable structure is adaptable to be delivered to the oral cavity in a constrained shape. The device can then undergo a conformation change in the oral cavity, where the device transforms into its unconstrained shape. The unconstrained shape of the device creates a useable working field in the oral cavity. The useable working field can provide increased accessibility to and/or visibility within the oral cavity. Also provided herein are methods for using the device and kits.

23 Claims, 34 Drawing Sheets

Related U.S. Application Data continuation of application No. 12/239,477, filed on Sep. 26, 2008, now abandoned.

(60) Provisional application No. 60/975,387, filed on Sep. 26, 2007, provisional application No. 61/026,989, filed on Feb. 7, 2008, provisional application No. 61/081,908, filed on Jul. 18, 2008.

(51) Int. Cl.
| | |
|---|---|
| *A61C 1/08* | (2006.01) |
| *A61C 17/06* | (2006.01) |
| *A61C 13/15* | (2006.01) |
| *A61B 1/06* | (2006.01) |
| *A61B 6/14* | (2006.01) |
| *A61C 9/00* | (2006.01) |
| *A61C 5/82* | (2017.01) |
| *A61C 5/90* | (2017.01) |

(52) U.S. Cl.
CPC ............... *A61C 1/088* (2013.01); *A61C 5/82* (2017.02); *A61C 5/90* (2017.02); *A61C 9/0033* (2013.01); *A61C 17/04* (2013.01); *A61C 19/003* (2013.01)

(58) Field of Classification Search
CPC ......... A61C 5/82; A61C 1/088; A61B 1/0684; A61B 1/24; A61B 1/32; A61B 6/14
See application file for complete search history.

(56) References Cited

U.S. PATENT DOCUMENTS

| | | | |
|---|---|---|---|
| 3,049,806 A * | 8/1962 | Cofresi | A61C 17/043 433/93 |
| 3,241,550 A | 3/1966 | Gelarie | |
| 3,332,417 A | 7/1967 | Blanford et al. | |
| 3,396,468 A | 8/1968 | Dayhoff | |
| 3,772,790 A | 11/1973 | Swan-gett et al. | |
| 3,781,994 A | 1/1974 | Hesselgren | |
| 3,916,880 A | 11/1975 | Schroer | |
| 4,002,162 A | 1/1977 | Weisser | |
| 4,019,255 A | 4/1977 | Cohen et al. | |
| 4,053,984 A | 10/1977 | Moss | |
| 4,179,815 A | 12/1979 | Hoffman | |
| 4,200,089 A | 4/1980 | Inoue | |
| 4,204,329 A | 5/1980 | Kahn | |
| 4,215,477 A | 8/1980 | Shanel | |
| 4,259,067 A | 3/1981 | Nelson | |
| 4,511,329 A | 4/1985 | Diamond | |
| 4,512,742 A | 4/1985 | Shanel | |
| 4,585,416 A | 4/1986 | DeNero | |
| 4,592,344 A * | 6/1986 | Scheer | A61B 1/07 433/29 |
| 4,600,387 A | 7/1986 | Ross | |
| 4,640,273 A | 2/1987 | Greene | |
| 4,671,260 A | 6/1987 | Buckner | |
| 4,695,253 A | 9/1987 | Tysse | |
| 4,744,758 A | 5/1988 | Harrison et al. | |
| 4,820,155 A | 4/1989 | Sauveur et al. | |
| 4,828,491 A | 5/1989 | Gray | |
| 4,889,490 A | 12/1989 | Jensen et al. | |
| 4,889,491 A | 12/1989 | Krygier et al. | |
| 4,899,490 A | 2/1990 | Jokel | |
| 4,952,143 A | 8/1990 | Becker et al. | |
| 4,984,564 A | 1/1991 | Yuen | |
| 5,011,409 A | 4/1991 | Gray | |
| 5,032,178 A | 7/1991 | Cornell | |
| 5,037,298 A * | 8/1991 | Hickham | A61C 5/90 433/93 |
| 5,078,604 A | 1/1992 | Malmin | |
| 5,090,047 A | 2/1992 | Angotti et al. | |
| 5,098,299 A | 3/1992 | Fischer | |
| 5,104,317 A | 4/1992 | Riazi | |
| 5,115,799 A | 5/1992 | McGann | |
| 5,190,546 A | 3/1993 | Jervis | |
| 5,199,872 A | 4/1993 | Leal | |
| 5,211,559 A | 5/1993 | Hart et al. | |
| 5,328,364 A | 7/1994 | Doyle | |
| 5,340,313 A | 8/1994 | Hussin | |
| 5,360,341 A | 11/1994 | Abramowitz | |
| 5,366,478 A | 11/1994 | Brinkerhoff et al. | |
| 5,460,524 A | 10/1995 | Anderson | |
| 5,466,153 A | 11/1995 | Poindexter | |
| 5,499,917 A | 3/1996 | Erickson et al. | |
| 5,513,986 A | 5/1996 | Feltham et al. | |
| 5,516,286 A | 5/1996 | Kushner | |
| 5,524,644 A | 6/1996 | Crook | |
| 5,590,504 A | 1/1997 | Heard et al. | |
| 5,632,284 A | 5/1997 | Graether | |
| 5,713,738 A | 2/1998 | Yarborough | |
| 5,730,597 A | 3/1998 | Luttrell | |
| 5,759,038 A | 6/1998 | Fischer | |
| 5,803,734 A | 9/1998 | Knutson | |
| 5,873,718 A | 2/1999 | Sullivan | |
| 5,879,159 A | 3/1999 | Cipolla | |
| 5,890,899 A | 4/1999 | Sclafani | |
| 5,931,673 A | 8/1999 | Bolbolan | |
| 5,964,770 A | 10/1999 | Flomenblit | |
| 6,017,304 A | 1/2000 | Vierra et al. | |
| 6,022,214 A | 2/2000 | Hirsch et al. | |
| 6,089,740 A | 7/2000 | Forehand et al. | |
| 6,102,701 A | 8/2000 | Engeron | |
| 6,116,900 A | 9/2000 | Ostler | |
| 6,162,055 A | 12/2000 | Montgomery et al. | |
| 6,193,513 B1 | 2/2001 | Pancallo | |
| 6,213,772 B1 * | 4/2001 | Costello | A61C 17/043 433/140 |
| 6,231,343 B1 | 5/2001 | Ishibashi et al. | |
| 6,254,534 B1 | 7/2001 | Butler et al. | |
| 6,267,591 B1 | 7/2001 | Barstow | |
| 6,309,625 B1 | 10/2001 | Jensen et al. | |
| 6,343,933 B1 | 2/2002 | Montgomery et al. | |
| 6,361,320 B2 | 3/2002 | Yarborough | |
| 6,391,283 B1 | 5/2002 | Jensen et al. | |
| 6,416,319 B1 | 7/2002 | Cipolla | |
| 6,416,322 B2 | 7/2002 | Qualliotine | |
| 6,436,034 B1 | 8/2002 | Funatogawa | |
| 6,450,983 B1 | 9/2002 | Rambo | |
| 6,485,301 B1 | 11/2002 | Germunder et al. | |
| 6,500,002 B2 | 12/2002 | Horiguchi | |
| 6,514,075 B1 | 2/2003 | Jacob | |
| 6,688,783 B2 | 2/2004 | Janosik et al. | |
| 6,692,250 B1 | 2/2004 | Decaudin et al. | |
| 6,712,608 B2 | 3/2004 | Bills et al. | |
| 6,716,029 B2 | 4/2004 | Fischer et al. | |
| 6,733,290 B2 | 5/2004 | West et al. | |
| 6,752,630 B2 | 6/2004 | Roetzer | |
| 6,773,290 B2 | 8/2004 | Lai | |
| 6,783,363 B2 | 8/2004 | Eguchi et al. | |
| D496,995 S | 10/2004 | Dorfman | |
| 6,805,127 B1 | 10/2004 | Karasic | |
| 6,880,954 B2 | 4/2005 | Ollett et al. | |
| D504,721 S | 5/2005 | Dorfman | |
| 6,923,761 B1 * | 8/2005 | Dorfman | A61B 1/24 433/140 |
| 6,974,321 B2 | 12/2005 | Hirsch et al. | |
| 6,981,870 B2 | 1/2006 | Heasley | |
| 6,988,893 B2 | 1/2006 | Haywood | |
| 7,040,894 B2 | 5/2006 | Horvath | |
| 7,077,652 B2 | 7/2006 | Kilcher et al. | |
| 7,300,401 B2 | 11/2007 | Patrickus | |
| D564,658 S | 3/2008 | Anderson | |
| D615,203 S | 5/2010 | Hirsch et al. | |
| D617,455 S | 6/2010 | Mori et al. | |
| D652,143 S | 1/2012 | Brown | |
| 8,376,743 B1 | 2/2013 | Bukhary | |
| 8,974,382 B2 | 3/2015 | Taljaard | |
| D737,964 S | 9/2015 | Jessop | |
| 2001/0012608 A1 | 8/2001 | Darnell | |
| 2001/0037053 A1 | 11/2001 | Bonadio et al. | |
| 2002/0022211 A1 | 2/2002 | Horiguchi | |
| 2003/0152196 A1 | 8/2003 | Bratslavsky et al. | |

(56) References Cited

U.S. PATENT DOCUMENTS

| | | |
|---|---|---|
| 2003/0198605 A1 | 10/2003 | Montgomery |
| 2004/0005529 A1 | 1/2004 | O'Neil |
| 2004/0033205 A1 | 2/2004 | Date et al. |
| 2004/0049099 A1 | 3/2004 | Ewers |
| 2004/0076926 A1 | 4/2004 | Baughman |
| 2004/0084826 A1 | 5/2004 | Kostiza |
| 2004/0097795 A1 | 5/2004 | Horvath |
| 2004/0152051 A1 | 8/2004 | Craig |
| 2004/0170945 A1 | 9/2004 | Heasley |
| 2004/0209224 A1* | 10/2004 | Heasley ............ A61C 5/82 433/139 |
| 2004/0209225 A1 | 10/2004 | Kilcher et al. |
| 2004/0219486 A1 | 11/2004 | Heasley |
| 2005/0048434 A1 | 3/2005 | Cipolla et al. |
| 2005/0064370 A1 | 3/2005 | Duret |
| 2005/0074720 A1 | 4/2005 | Anderson |
| 2005/0171406 A1 | 8/2005 | Dorfman et al. |
| 2005/0186535 A1 | 8/2005 | Bills et al. |
| 2005/0227199 A1 | 10/2005 | Patrickus |
| 2005/0265933 A1 | 12/2005 | Montgomery et al. |
| 2006/0003284 A1 | 1/2006 | Sale et al. |
| 2006/0069316 A1 | 3/2006 | Dorfman et al. |
| 2006/0115789 A1 | 6/2006 | Wishart |
| 2006/0155171 A1* | 7/2006 | Yang ............ A61B 1/0676 600/238 |
| 2006/0234187 A1 | 10/2006 | Kilcher et al. |
| 2007/0148619 A1 | 6/2007 | Anderson |
| 2007/0231773 A1 | 10/2007 | Pontynen et al. |
| 2007/0270965 A1 | 11/2007 | Ferguson |
| 2008/0064001 A1 | 3/2008 | Dorfman et al. |
| 2008/0153058 A1 | 6/2008 | Horvath |
| 2009/0081611 A1 | 3/2009 | Hines et al. |
| 2011/0060194 A1 | 3/2011 | Risto et al. |
| 2012/0012120 A1 | 1/2012 | Giffey |
| 2013/0230822 A1 | 9/2013 | Hines |
| 2016/0008094 A1 | 1/2016 | Jessop et al. |
| 2016/0022381 A1 | 1/2016 | Jessop et al. |
| 2016/0270880 A1 | 9/2016 | Hines et al. |

FOREIGN PATENT DOCUMENTS

| | | |
|---|---|---|
| CN | 2416869 | 1/2001 |
| CN | 200963161 | 10/2007 |
| CN | 101299956 | 11/2008 |
| CN | 202262973 | 6/2012 |
| CN | 202408831 | 9/2012 |
| CN | 202590146 | 12/2012 |
| EP | 1455636 B1 | 4/2009 |
| JP | S51-797 | 1/1976 |
| JP | H1-69510 | 5/1989 |
| JP | 2002017670 | 1/2002 |
| JP | 2005511232 T2 | 4/2005 |
| JP | 3851631 B2 | 11/2006 |
| JP | 2007-209635 | 8/2007 |
| JP | 2007-283094 | 11/2007 |
| JP | 2010-540117 | 12/2010 |
| JP | 2012-254212 | 12/2012 |
| KR | 1019980087815 | 12/1998 |
| KR | 20-0359447 | 8/2004 |
| WO | WO 0207636 A1 | 1/2002 |
| WO | WO03051185 A1 | 6/2003 |
| WO | WO04075927 A2 | 9/2004 |
| WO | WO2007115144 A2 | 10/2007 |
| WO | WO2007115144 A3 | 10/2007 |
| WO | WO2009042957 A2 | 4/2009 |
| WO | WO2009042957 A3 | 5/2009 |

OTHER PUBLICATIONS

U.S. Appl. No. 60/975,387, filed Sep. 26, 2007, Pontynen.
U.S. Appl. No. 61/789,929, filed Mar. 15, 2013, Jessop et al.
U.S. Appl. No. 29/485,036, filed Mar. 14, 2014, Jessop et al.
U.S. Appl. No. 29/532,890, filed Jul. 10, 2015, Jessop et al.
U.S. Appl. No. 29/533,704, filed Jul. 21, 2015, Jessop et al.
U.S. Appl. No. 29/563,114, filed May 2, 2016, Jessop et al.
U.S. Appl. No. 29/567,628, filed Jun. 10, 2016, Jessop et al.
Isolite Systems. Isolite i2. Available at: www.isolitesystems.com. Accessed on Oct. 21, 2008.
Kerr Corporation. Consumale Dental Restorative Materials Manufacturer. Available at: www.kerrhawe.com Accessed on Oct. 21, 2008.
Ivoclar Vivadent Inc. OptraDam Available at: www.ivoclar.co.nz. Accessed on Oct. 21, 2008.
OptiDAm. Available at www.kerrhawe.com. Accessed Jul. 10, 2007.
OptraGate. Available at www.ivoclar.co.nz. Accessed Jul. 10, 2007.
Dentapops. Available at http://dynaflex.com/en-us/dept_329.html. Accessed Jul. 10, 2007.
Drysolator: Dental Dry Isolator. Available at http://drysolator.com/index.html. Accessed on Jul. 31, 2007 (2 pages).
Full Arch Dry Field System. Available at http://www.nolaspecialties.com/fulardryfiel.html. Accessed on Jul. 31, 2007 (1 Page).
Notice of Rejection in Japanese Patent Application No. 2010-527217 dated Mar. 11, 2014, acting as English Translation of cited reference JP H1-69510.
U.S. Appl. No. 12/239,477, filed Apr. 22, 2011, Office Action.
U.S. Appl. No. 12/239,477, filed Nov. 14, 2011, Office Action.
U.S. Appl. No. 12/239,477, filed Feb. 12, 2013, Office Action.
U.S. Appl. No. 12/239,477, filed Sep. 23, 2013, Office Action.
U.S. Appl. No. 13/829,609, filed Jun. 25, 2014, Office Action.
U.S. Appl. No. 13/829,609, filed Nov. 26, 2014, Office Action.
U.S. Appl. No. 29/485,036, filed Jun. 24, 2015, Notice of Allowance.
U.S. Appl. No. 13/829,609, filed Dec. 16, 2015, Office Action.
U.S. Appl. No. 29/533,704, filed Jan. 20, 2016, Office Action.
U.S. Appl. No. 29/532,890, filed Mar. 18, 2016, Notice of Allowance.
U.S. Appl. No. 13/829,609, filed Mar. 29, 2016, Notice of Allowance.
U.S. Appl. No. 29/533,704, filed Apr. 8, 2016, Notice of Allowance.
Supplementary European Search Report issued in European Application No. EP14763277, dated Oct. 20, 2016.
U.S. Appl. No. 14/776,867, filed Nov. 17, 2016, Office Action.
Office Action dated Dec. 2, 2016 cited in U.S. Appl. No. 29/563,114.
Office Action dated May 5, 2017 cited in U.S. Appl. No. 14/776,867.
Office Action issued in JP Patent Application No. 2016-502701 dated Mar. 1, 2017.
U.S. Appl. No. 29/563,114, filed Mar. 13, 2017, Notice of Allowance.
Notice of Allowance dated Oct. 13, 2017 cited in U.S. Appl. No. 14/776,867.
Office Action dated Oct. 23, 2017 cited in U.S. Appl. No. 14/858,954.

* cited by examiner

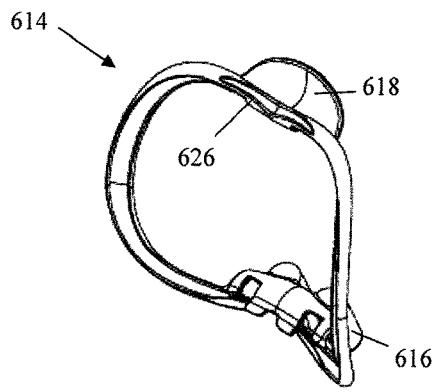
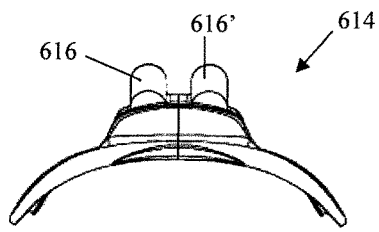
FIG. 6A        FIG. 6B
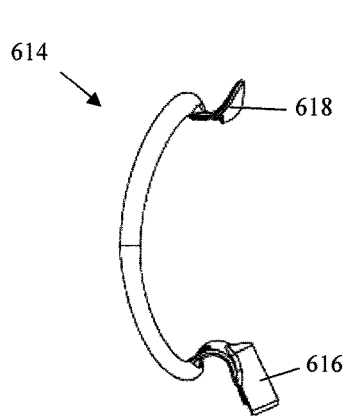
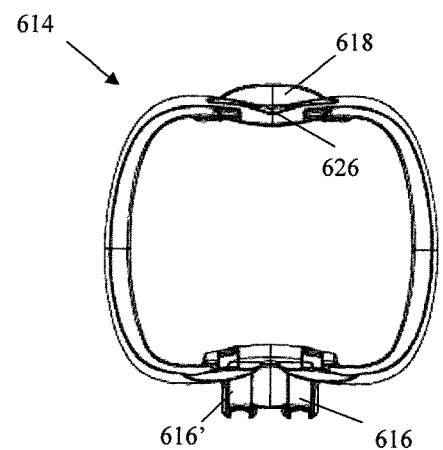
FIG. 6C        FIG. 6D

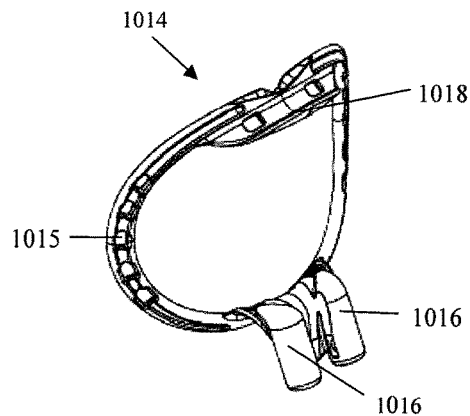
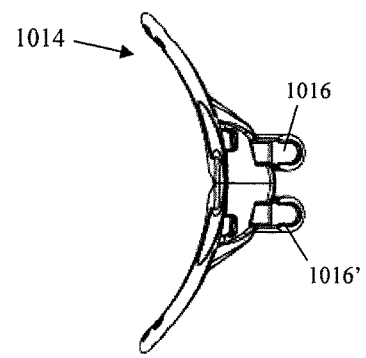
FIG. 10A          FIG. 10B
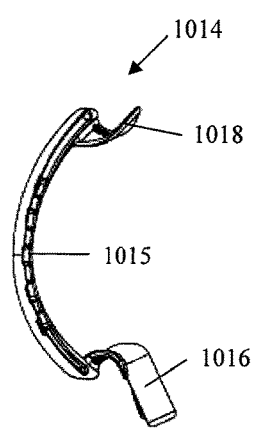
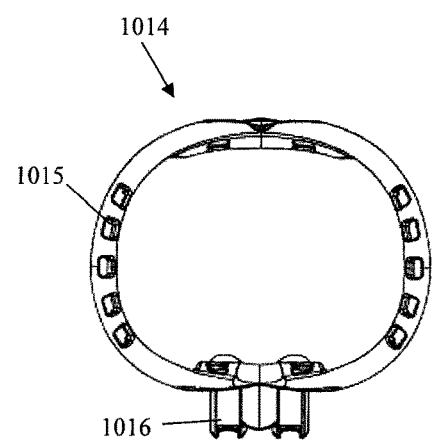
FIG. 10C          FIG. 10D

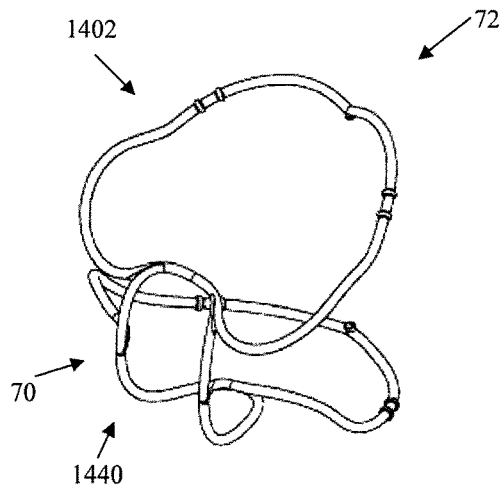
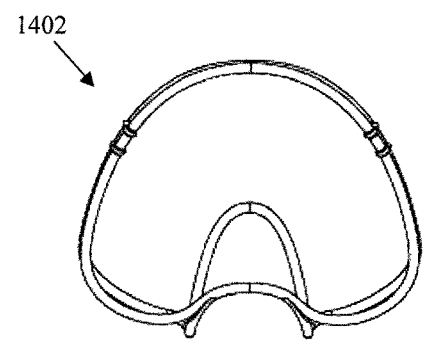
FIG. 14A  FIG. 14B
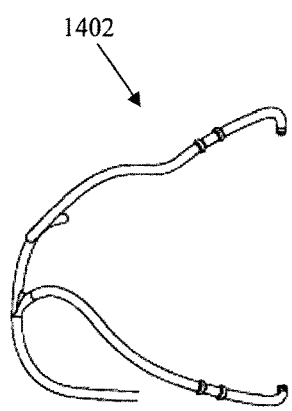
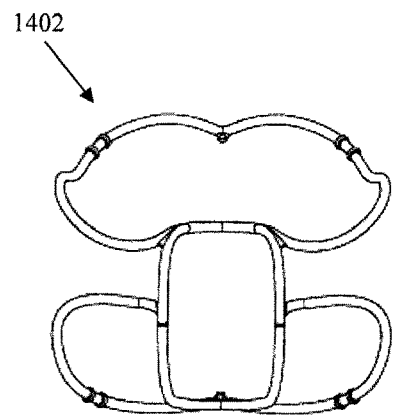
FIG. 14C  FIG. 14D

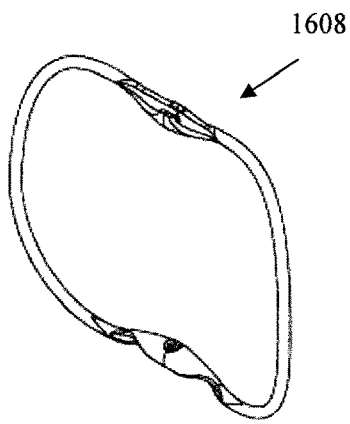
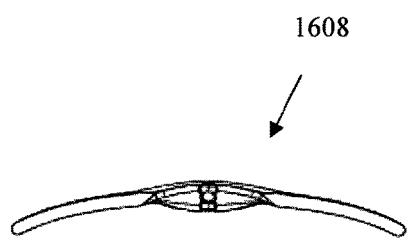
FIG. 16A
FIG. 16B
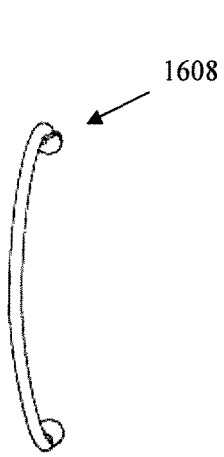
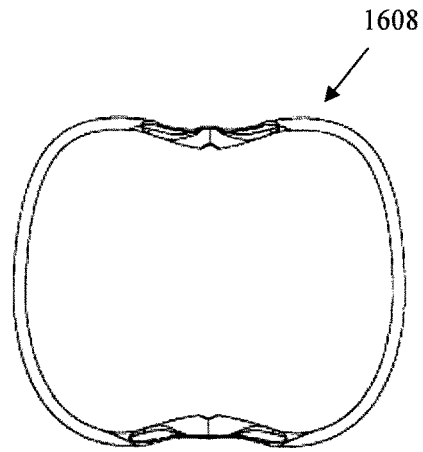
FIG. 16C
FIG. 16D

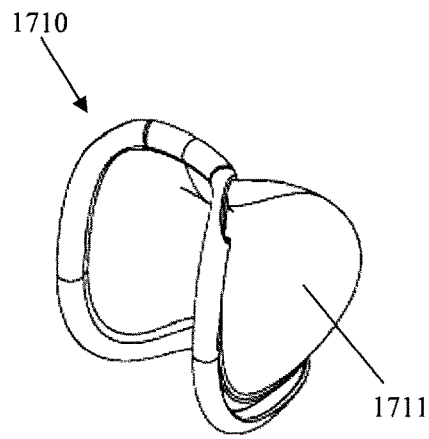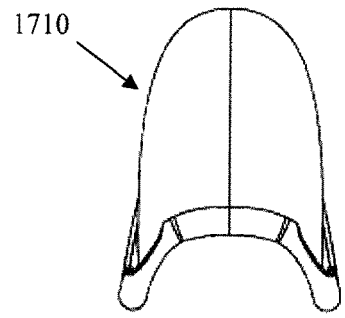
FIG. 17A  FIG. 17B
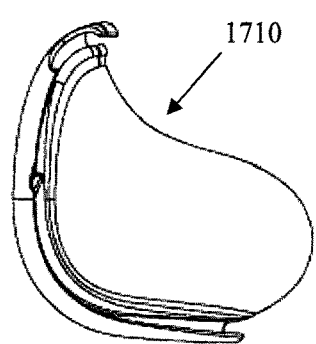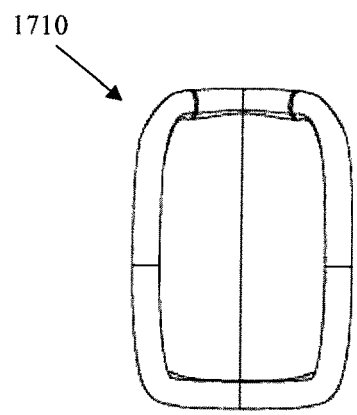
FIG. 17C  FIG. 17D

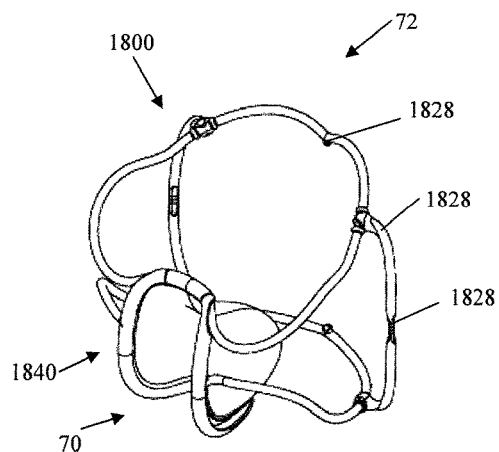
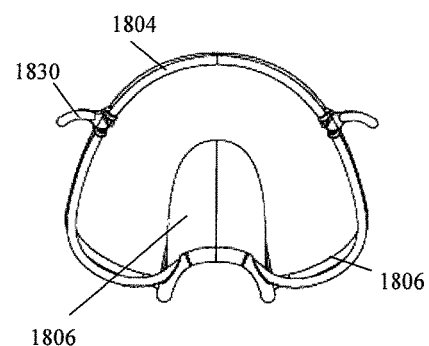
FIG. 18A
FIG. 18B
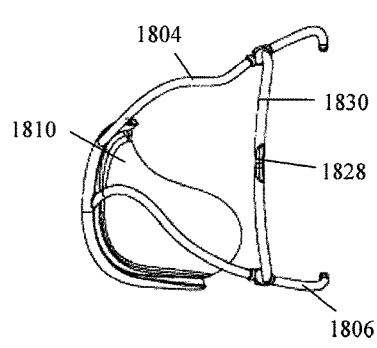
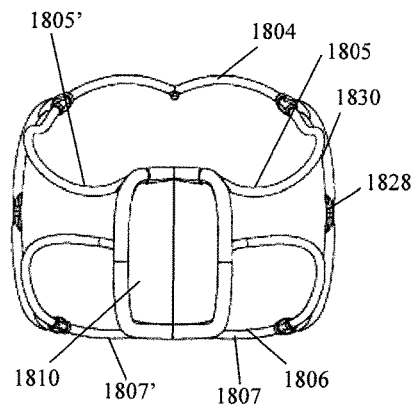
FIG. 18C
FIG. 18D

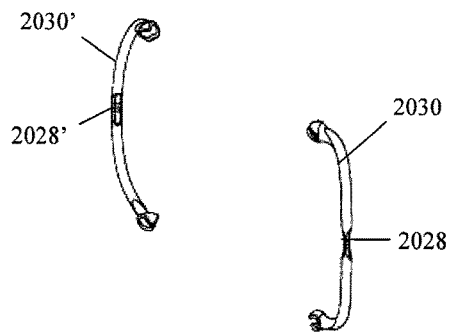 
FIG. 20A  FIG. 20B
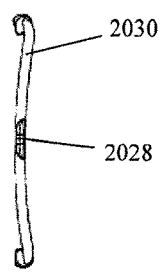 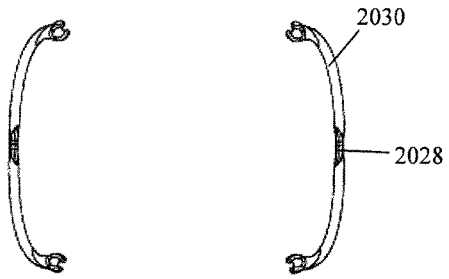
FIG. 20C  FIG. 20D

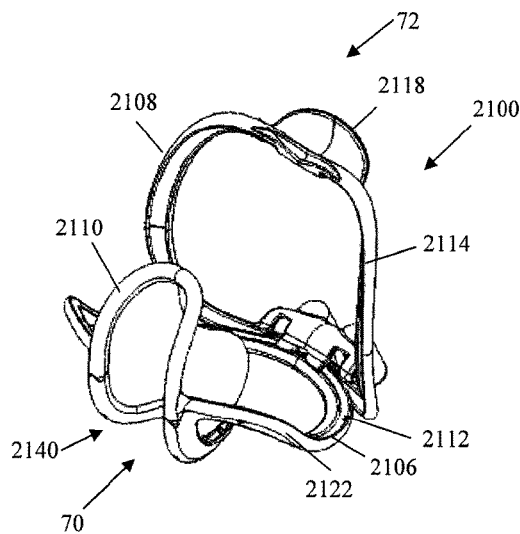
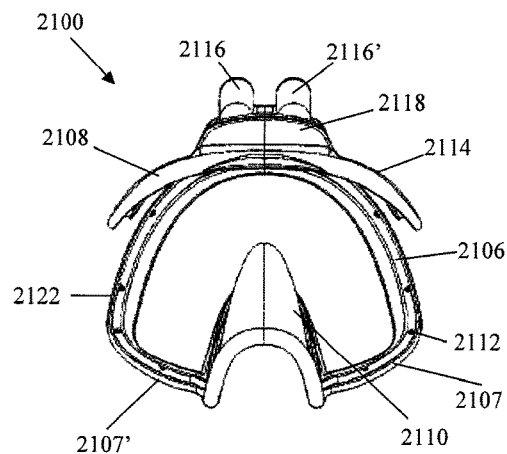
FIG. 21A  FIG. 21B
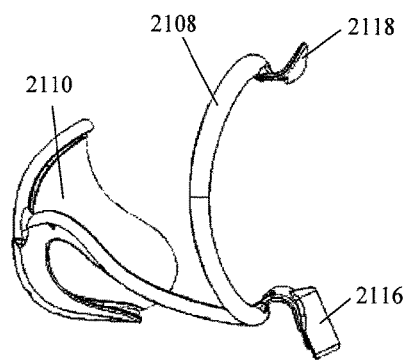
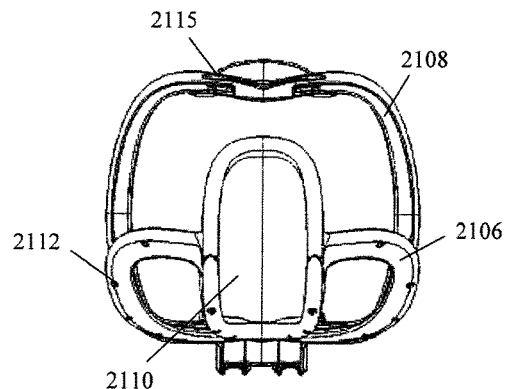
FIG. 21C  FIG. 21D

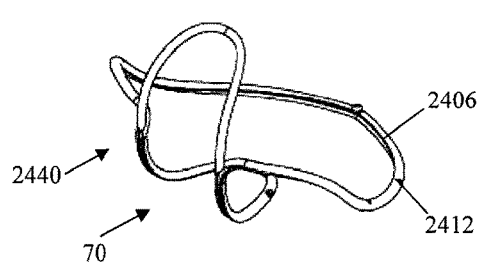
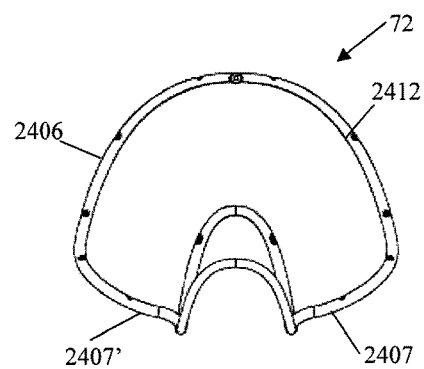
FIG. 24A  FIG. 24B
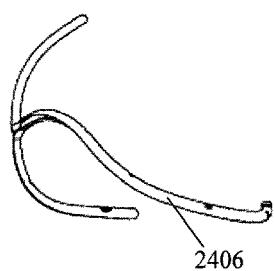
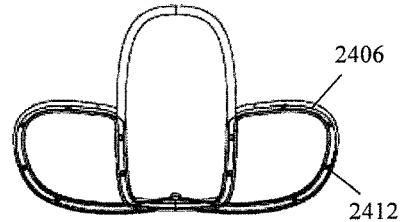
FIG. 24C  FIG. 24D

METHODS, DEVICES, SYSTEMS, ASSEMBLIES, AND KITS FOR TISSUE RETRACTION IN AN ORAL CAVITY

CROSS-REFERENCE TO RELATED APPLICATIONS

This application is a continuation of U.S. patent application Ser. No. 13/829,609, filed Mar. 14, 2013, which is a continuation of U.S. patent application Ser. No. 12/239,477, filed Sep. 26, 2008, now abandoned, which claims the benefit of U.S. Provisional Application No. 60/975,387, filed Sep. 26, 2007, U.S. Provisional Application No. 61/026,989, filed Feb. 7, 2008, and U.S. Provisional Application No. 61/081,908, filed Jul. 18, 2008, the disclosures of which are incorporated herein in their entirety.

BACKGROUND OF THE INVENTION

The mouth or oral cavity 10 of a human is illustrated in FIG. 1A to provide context for the invention. The mouth, or oral cavity, is bounded by muscles and bones: anteriorly by the lips 12, posteriorly continuous with the oropharynx, laterally by the muscles of the cheeks 14, superiorly by the body hard palate and muscular soft palate 16; and inferiorly by the muscular tongue 18 and the soft tissues of the floor of the mouth. The tongue is a voluntary muscular structure that occupies the floor of the mouth. Teeth 20 are embedded in the alveoli or sockets of alveolar ridges of the mandible 30 which forms a mandibular arch 32, or alveolar process, which contain the lower (caudad) set of teeth and maxilla 40 which forms a maxillary arch 42, or alveolar process, which contains the upper (cephalad) set of teeth. Each of the alveolar arch 32, 42, has an external surface 34, 44 which is adjacent the checks and lips and an internal surface 36, 46 adjacent the tongue and palate. The teeth 20 engage the gingival tissue 22.

The mouth 10 has salivary glands that secrete about 1.5 L of fluid daily into the mouth. Secretion of saliva is controlled by the autonomic nervous system. Parasympathetic stimulation causes vasodilation and secretion of water saliva with low enzyme content, whereas sympathetic stimulation cases vasoconstriction and secretion of smaller amounts of saliva that are richer in organic materials. Reflex secretion occurs when, for example, there is food in the mouth.

Devices and systems currently known and used in the dental arts include those disclosed in: U.S. Pat. No. 4,695,253 to Tysse for Oral Evacuation Device and Method; U.S. Pat. No. 6,981,870 to Heasley for Rubber Dam Clamps Retained by Adhesion and Improved Frictional Forces; U.S. Pat. No. 6,022,214 to Hirsch et al. for Intraoral Illumination Device and Method of Using Same; U.S. Pat. No. 5,931,673 to Bobolan for Intraoral Dental Dam; U.S. Pat. No. 5,890,899 to Sclafani for Dental Isolator; U.S. Pat. No. 5,516,286 to Kushner for Dental Isolation Tray Particularly Suited for Use When Applying Dental Sealants and Method for Its Use; U.S. Pat. No. 5,460,524 to Anderson for Device and Method for Saliva Suction with Tongue Retractor and Bit Handle; U.S. Pat. No. 5,078,604 to Malmin for Dental Barrier Drape Devices and Retainer Apparatus Therefor; U.S. Pat. No. 5,037,298 to Hickham for Apparatus and Improves Process for Removing Saliva While Retracting Cheeks and Lips; U.S. Pat. No. 4,899,490 to Jenkinson for Dental Mask; U.S. Pat. No. 4,215,477 to Shanel for Holder for Rubber Dental Dam; U.S. Pat. No. 3,772,790 to Swan-Gett et al. for Tooth Isolating Shield; U.S. Patent Publication US 2004/0170945 to Heasley for General Field Isolation Rubber Dams without Operative Inserts Which Isolate the Dental Alveolar Arch for Dental Treatment; and US 2007/0231773 to Pontynen et al. for Methods, Devices, Systems, and Kits for Isolating Teeth.

Commercially available devices include, for example, Isolite i2 by Isolyte Systems (Santa Barbara, Calif.), described at www.isolitesystems.com; OptiDam by KerrHawe SA (Switzerland), described at www.kerrhawe.com; and OptraGate and OptraDam by IvoClar Vivident Ltd. (New Zealand), described at www.ivoclar.co.nz.

It would be beneficial to have a device, system, assembly, kit and method that enables dental practitioners to quickly retract tissue and isolate one or more teeth and/or gingival tissue in the oral cavity from surrounding tissue to generate a working field and which maintains a dry working field for performing the dental procedure.

SUMMARY OF THE INVENTION

Provided herein is a retraction device comprising a topology conformable structure adaptable to be in a constrained shape that can be delivered into an oral cavity and further adaptable to be in an unconstrained shape to create a useable working field in the oral cavity, the useable working field providing increased accessibility and increased visibility within the oral cavity. In some embodiments, the conformable structure is a frame. Additionally, the frame can further comprise a membrane. The frame can also comprise a light source. The frame can also comprise an evacuation component. The device can be adaptable to be deployed in under 1 minute. In some embodiments, the device can be adaptable to create a working field in under 1 minute. The device can be deployed in under 20 seconds. The device can further comprise a tongue retractor wherein the tongue retractor can be adaptable to deflect the tongue without passing over either arch of teeth. The tongue retractor can contain and confine the tongue in a restricted space. In some embodiments, the device can further comprise at least one evacuation component. The evacuation component can be used to remove saliva or other bodily fluids from the oral cavity. Additionally, the evacuation component can be used to remove moist air or breath from the oral cavity. The device can be adaptable to retract soft tissue surrounding at least one arch of teeth. Additionally, the device can be adaptable to retract the soft tissue surrounding both the upper and lower arches of teeth in the oral cavity. The device can also be used in some cases to isolate at least a portion of gum tissue in the oral cavity. In isolating the teeth of gum tissue, the device can be used to create a barrier that can be efficiently separate dental surfaces from any influence by saliva or other body fluids. Furthermore, the device can comprise at least one aperture to facilitate the ability to breathe through the device. The device can facilitate the scanning of the dental surfaces by providing increased accessibility to the oral cavity and increased visibility within the structures within the oral cavity. The device can facilitate scanning or imaging of the oral cavity, wherein the scanning or imaging comprises at least one of digital scanning/imaging or optical scanning/imaging. Furthermore, the device can be adaptable to isolate both arches of teeth is less then 20 seconds. In some embodiments, the device can be adaptable to be positioned without interfering with access to dental surfaces, while also being further adaptable to prevent interference with access to dental surfaces by the tongue, cheeks or lips and further adaptable to provide maximum patient comfort.

Further provided herein is a retraction device comprising a topology conformable structure adaptable to create a working field in an oral cavity of a patient, wherein the working field is at least 10% larger than a working field created in the oral cavity of the patient without use of the device. The device can be used to provide at least 10% more access to an area of interest in the oral cavity. In some embodiments, the area of interest is one arch of teeth. Alternatively, the area of interest can be both arches of teeth. The device can be adaptable to provide at least 10% more visibility within the oral cavity. The device can be adaptable to provide at least 10% less contamination of structures located in the oral cavity by fluid. The fluid can be saliva, blood, or any other suitable bodily fluid. In some embodiments, the device can be adaptable to provide at least 10% less interference by soft tissue in accessing structures in the oral cavity. The conformable structure can be a frame. The device can be adaptable to evacuate bodily fluids from a protected side of the oral cavity and also any fluid used to rinse the oral cavity on the working field side of the membrane during a procedure. In some embodiments, the device can comprise a full membrane that can isolate the oral cavity from harmful debris or undesirable chemicals and tastes. In some embodiments, the frame is a wire frame. In some embodiments, the device further comprises a membrane. Additionally, the device can comprise a light source. The light source can be used to illuminate the oral cavity. The light source can be used to cure materials placed in the oral cavity. Alternatively, the device can comprise light sources that can either illuminate or cure material. The device can be adaptable to isolate at least one arch located within the oral cavity or create a barrier that can efficiently separate dental surfaces from any influence by saliva or other bodily fluid. The device can be adaptable to isolate the upper arch and the lower arch in the oral cavity. In some embodiments, the device can be adaptable to isolate at least a portion of gum tissue in the oral cavity. The device can be used to isolate the entire gum tissue. Furthermore, the device can be adaptable to be deployed in under 1 minute. The device can also be adaptable to create a working field in under 1 minute. In some embodiments, the device can be deployed in under 20 seconds. Additionally, no further adjustment of the device can be needed after the device has been deployed. In some embodiments, the device can further comprise a tongue retractor. The tongue retractor can contain and confine the tongue in a restricted space. The tongue retractor and the elements which attach it to the rest of the device can be adaptable to allow a first occlusal surface of a tooth in the upper arch of teeth and a second occlusal surface of a tooth in the lower arch of teeth to touch. The tongue retractor can be adaptable to compress at least one side of the tongue or both sides of the tongue. The device can be adaptable to apply suction to the oral cavity. The device can be adaptable to apply suction to the oral cavity through at least one aperture. The device can also be adaptable to facilitate the ability to breathe through the device. The device can be adaptable to isolate at least one dental arch or create a barrier around the at least one dental arch in less than 20 seconds. The device can further be adaptable to be positioned without interfering with access to dental surfaces and further adaptable to provide maximum patient comfort.

Additionally, provided herein is a retraction device comprising a malleable frame adaptable to be in a constrained shape that can be delivered into an oral cavity and further adaptable to be in an unconstrained shape to isolate at least one arch of teeth from saliva and soft tissue surrounding the arch. The malleable frame can be a wire frame, including but not limited to a metal wire. Alternatively, the wire frame can be a polymer frame or a combination or metal and polymer frame. The malleable frame can further comprise a membrane. Additionally, the device can further comprise a light source. In some embodiments, the device can be adaptable to be deployed in under 1 minute, The device can be adaptable to be deployed in under 20 seconds, in some embodiments. The device can also be adaptable to create a working field in under 1 minute. Furthermore, the device can comprise a tongue retractor. The tongue retractor can contain and confine the tongue. The tongue retractor and the elements which attach it to the rest of the device can be adaptable to allow a first occlusal surface of a tooth in the upper arch of teeth and a second occlusal surface in the lower arch of teeth to touch. The device can also comprise at least one evacuation component. The device can be adaptable to retract soft tissue surrounding at least one arch of teeth or in some cases, retract the soft tissue surrounding the upper and lower arches of teeth. The device can be adaptable to isolate at least a portion of gum tissue located in the oral cavity. In some embodiments, the device further comprises at least one aperture to facilitate the ability to breathe through at least one aperture in the device. The device can be further adaptable to facilitate the application of a substance to at least one tooth surface. The substance can be a powder. In some embodiments, the powder is a reflective powder. The powder can be an imaging powder for pattering the dental surfaces. The substance can be a dental restorative material or medication. The device can also be adaptable to facilitate the application of hardware (orthodontic brackets) to at least one tooth surface. The device can be further adaptable to facilitate treatment of at least one periodontal pocket using including, but not limited to, a laser device, an ultrasonic or sonic frequency scaler device, treatment with hand scalers and curettes, periodontal surgery, or dental implant placement, or any suitable combination thereof The device can also be adaptable to isolate at least one dental arch in less than 20 seconds. The device can be adaptable to create a working field without interfering with access to dental surfaces. The device can be further adaptable to be positioned in the mouth to provide for maximum patient comfort.

Further provided herein are methods of use of the invention described herein. Provided herein is a method of retracting tissue in an oral cavity comprising: inserting a retraction device comprising a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity; and positioning the retraction device in the oral cavity to create the useable working field. The positioning step can be performed in less than 1 minute. In some embodiments, the positioning step can be performed in less than 20 seconds.

Yet another method for retracting tissue in an oral cavity comprises: inserting a retraction device comprising a topology conformable structure adaptable to create a useable working field in an oral cavity of a patient, wherein the working field is at least 10% larger than a working field in oral cavity of the patient without use of the device; and positioning the retraction device in the oral cavity to create the working field.

Another method provided herein is a method of facilitating the creation of an oral cavity model comprising: inserting a retraction device comprising a topology conformable structure adaptable to be in a constrained shape that can be delivered into an oral cavity and further adaptable to be in an unconstrained shape to create a useable working field in the oral cavity, the usable working field providing increased accessibility to and increased visibility within the oral cavity; and positioning the retraction device in the oral cavity to create the useable working field in the oral cavity. In some embodiments, the method can further comprise the step of illuminating the oral cavity with the retraction device. Additionally, the method can comprise the step of applying an imaging powder to the at least one dry tooth surface.

Further provided herein are kits for retracting tissue in an oral cavity. Provided herein are kits for retracting tissue in an oral cavity comprising: a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity. In some embodiments, the kit can further comprise a tongue retractor. Additionally, the kit can further comprise a light ring. Furthermore, the kit can comprise an evacuation component. The kit can further comprise a membrane adaptable to be fitted over the frame. In some embodiments, the kit can further comprise a gum protection cover. The kit can also further comprise a lip ring.

Furthermore, additionally provided herein is a kit for retracting tissue in an oral cavity comprising: a retraction device comprising a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity; and a kit of secondary dental products wherein tissue retraction in the oral cavity is necessary. In some embodiments, the kit can further comprise an illumination source. Additionally, the kit can comprise at least one optical scanner or digital scanner. Furthermore, the kit can further comprise a powder for facilitate scanning of the dental surfaces. In some embodiments, the kit can further comprise a whitening or bleaching kit.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A is a perspective view of the device positioned in the oral cavity; FIG. 2B is a side view of the retraction device positioned within the oral cavity; FIG. 2C depicts a portion of the retraction device positioned over the caudad portion of the oral cavity as viewed along the line B-B in FIG. 2B;

FIG. 2D depicts a portion of the retraction device positioned over the caudad portion of the oral cavity as viewed along the line B-B in FIG. 2B, without surrounding tissue structures; FIG. 2E depicts a portion of the retraction device positioned over the cephalad portion of the oral cavity as viewed along the line B-B in FIG. 2B.

FIG. 3A is perspective view of the retraction device as viewed from the distal end of the device; FIG. 3B is a top view of the retraction device; FIG. 3c is a side view of retraction device; FIG. 3D is a posterior view of the retraction device;

FIG. 4A is a perspective view of the tongue and gum protection cover of the retraction device as viewed from the distal end of the device; FIG. 4B is a top view of the tongue and gum protection cover of the retraction device; FIG. 4C is a side view of the tongue and gum protection cover of the retraction device;

FIG. 4D is a posterior view of the tongue and gum protection cover of the retraction device;

FIG. 5A is a perspective view of the frame as viewed from the distal end of the device; FIG. 5B is a top view of the frame of the retraction device;

FIG. 5C is a side view of the frame of the retraction device; FIG. 5D is a posterior view of the frame of the retraction device;

FIGS. 6A-6D illustrate the light ring portion of the retraction device isolated from the retraction device; FIG. 6A illustrates a perspective view of the light ring as viewed from the posterior side; FIG. 6B illustrates a top view of the light ring; FIG. 6C illustrates a side view of the isolated light ring; FIG. 6D illustrates a posterior view of the light ring;

FIG. 7A illustrates the retraction device as viewed from the distal end of the device; FIG. 7B illustrates a top view of the retraction device; FIG. 7C illustrates a side view of the retraction device; FIG. 7D illustrates a posterior view of the retraction device;

FIG. 8A illustrates a perspective view of the isolation/retraction device; FIG. 8B illustrates a top view of the isolation/retraction device; FIG. 8C illustrates a side view of the isolation/retraction device; FIG. 8D illustrates a posterior view of the isolation/retraction device;

FIG. 9A illustrates a perspective view of the isolation membrane of the retraction device; FIG. 9B illustrates a top view of the isolation membrane of the retraction device; FIG. 9C illustrates a side view of the isolation membrane/cover of the retraction device; FIG. 9D illustrates a posterior view of the isolation membrane/cover of the retraction device;

FIGS. 10A-10D illustrate an alternative embodiment of a light ring and lip and cheek retractor isolated from a retraction device; FIG. 10A illustrates a perspective view of the light ring; FIG. 10B illustrates a top view of the isolated light ring; FIG. 10C illustrates a side view of the isolated light ring;

FIG. 10D illustrates a posterior view of the isolated light ring;

FIG. 11A illustrates a perspective view of the light ring; FIG. 11B illustrates a top view of the isolated light ring; FIG. 11C illustrates a side view of the isolated light ring; FIG. 11D illustrates a posterior view of the isolated light ring;

FIG. 12A illustrates a perspective view of the frame; FIG. 12B illustrates a top view of an isolated frame; FIG. 12C illustrates a side view of an isolated frame; FIG. 12D illustrates a posterior view of the isolated frame;

FIG. 13A illustrates a perspective view of the frame; FIG. 13B illustrates a top view of an isolated frame of the retraction device; FIG. 13C illustrates a side of the frame; FIG. 13D illustrates a posterior view of the isolated frame;

FIGS. 14A-14D illustrate an isolated view an alternative embodiment of a frame; FIG. 14A illustrates a perspective view of the frame; FIG. 14B illustrates a top view of the frame; FIG. 14C illustrates a side view of the frame; FIG. 14D illustrates an posterior view of the frame;

FIG. 15S illustrates a perspective view of the frame; FIG. 15B illustrates a top view of the frame; FIG. 15C illustrates a side view of the frame; FIG. 15D illustrates an posterior view of the frame;

FIGS. 16A-16D illustrate an alternative embodiment of an isolated lip ring; FIG. 16A illustrates a perspective view of the lip ring as viewed from the distal side; FIG. 16B illustrates a top view of the lip ring; FIG. 16C illustrates a side view of the lip ring; FIG. 16D illustrates a posterior view of the lip ring;

FIGS. 17A-17D illustrate an embodiment of an isolated tongue cover; FIG. 17A illustrates a perspective view of the tongue cover; FIG. 17B illustrates a top view of a tongue cover; FIG. 17C illustrates a side view of a tongue cover; FIG. 17D illustrates a posterior view of a tongue cover;

FIGS. 18A-18D illustrates an alternate embodiment of an frame adaptable to be folded; FIG. 18A illustrates a perspective view of the frame as viewed from the distal end; FIG. 18B illustrates a top view of the frame; FIG. 18C illustrates a side view of the frame; FIG. 18D illustrates a posterior view of the frame;

FIG. 19A illustrates a perspective view of the frame as viewed from the distal end; FIG. 19B illustrates a top view of the frame; FIG. 19C illustrates a side view of the frame; FIG. 19D illustrates a posterior view of the frame;

FIGS. 20A-20D illustrate isolated cheek retractors from a foldable frame; FIG. 20A illustrates a perspective view of the cheek retractors; FIG. 20B illustrates a top view of the cheek retractors; FIG. 20C illustrates a side view of the cheek retractors; FIG. 20D illustrates a posterior view of the cheek retractors;

FIGS. 21A-21D illustrate a retraction device for retracting tissue surrounding the lower arch, tongue, cheeks, and lips, including lighting and suction; FIG. 21A illustrates a perspective view of the retraction device as viewed from the distal side; FIG. 21B illustrates the retraction device as viewed from top; FIG. 21C illustrates a side view of the retraction device; FIG. 21D illustrates a posterior view of the retraction device;

FIG. 22A illustrates a perspective view of the retraction device as viewed from the distal side; FIG. 22B illustrates a top view of the retraction device; FIG. 22C illustrates a side view of a retraction device; FIG. 22D illustrates a posterior view of a retraction device;

FIG. 23A illustrates a perspective view of the retraction device as viewed from the distal end; FIG. 23B illustrates a top view of the retraction device; FIG. 23C illustrates a side view of the retraction device; FIG. 23D illustrates a posterior view of the retraction device;

FIGS. 24A-24D illustrate an isolated view of an alternate embodiment of a frame comprising an evacuation component; FIG. 24A illustrates a perspective view of the frame as viewed from the distal end; FIG. 24B illustrates a top view of the frame; FIG. 24C illustrates a side view of the frame; FIG. 24D illustrates a posterior view of the frame;

FIG. 25A illustrates a perspective view of the retraction device as viewed from the distal end; FIG. 25B illustrates a top view of the frame; FIG. 25C illustrates a side view of the frame; FIG. 25D illustrates a posterior view of the frame;

FIG. 26A illustrates a perspective view of the retraction device; FIG. 26B illustrates a top view of the retraction device; FIG. 26C illustrates a side view of the retraction device; FIG. 26D illustrates a posterior view of the retraction device;

FIG. 27A is a perspective view of the frame as viewed from the front; FIG. 27B illustrates a top view of the retraction device; FIG. 27C illustrates a side view of the retraction device; FIG. 27D illustrates a view of the retraction device as viewed from the top;

FIG. 28A illustrates a perspective view of the frame as viewed from the distal side; FIG. 28B illustrates a top view of the frame; FIG. 28C illustrates a side view of the frame; FIG. 28D illustrates a posterior view of the frame;

FIG. 29A illustrates a perspective view of the tongue cover as viewed from the distal side; FIG. 28B illustrates a top view of the tongue cover; FIG. 29C illustrates a side view of the tongue cover; FIG. 29D illustrates a posterior view of the tongue cover;

FIG. 30A illustrates a perspective view of the frame; FIG. 30B illustrates a top view of frame; FIG. 30C illustrates a side view of the frame; FIG. 30D illustrates a posterior view of the frame;

FIG. 31A illustrates a perspective view of the frame; FIG. 31B illustrates a top view of frame; FIG. 31C illustrates a side view of the frame; FIG. 31D illustrates a frontal view of the frame; FIG. 32A illustrates a perspective view of the frame; FIG. 32B illustrates a top view of frame; FIG. 32C illustrates a side view of the frame; FIG. 32D illustrates a frontal view of the frame.

DETAILED DESCRIPTION OF THE INVENTION

Figure 1A:
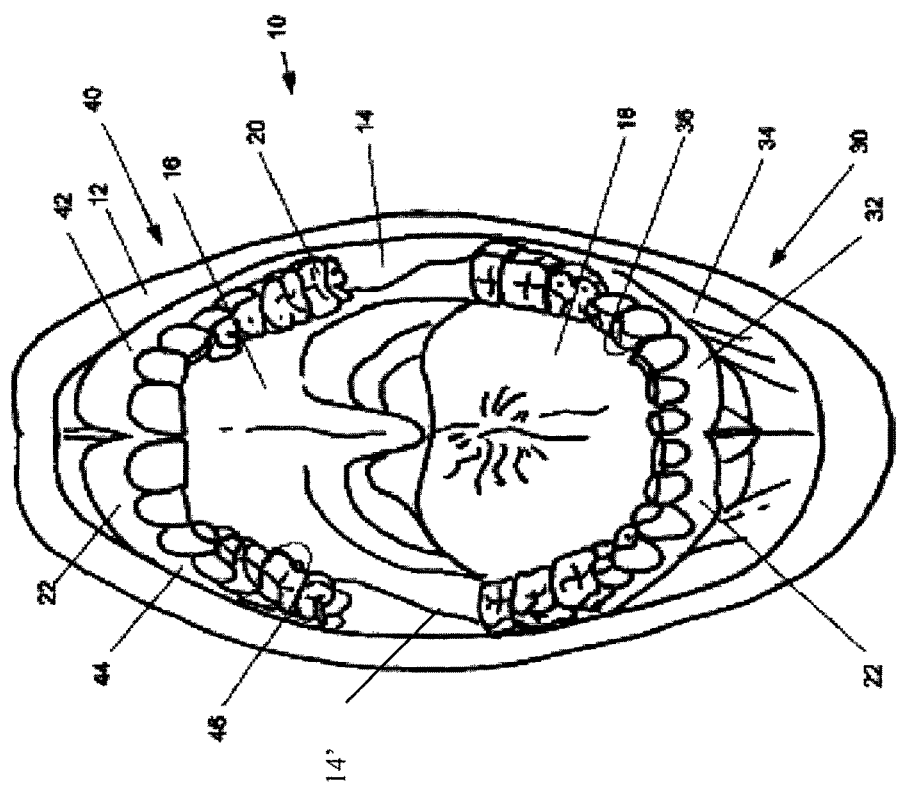
FIG. 1A depicts an anterior view of an oral cavity with the mouth open and the teeth exposed illustrating the structures of the oral cavity.

In order to understand the configurability, adaptability and operational aspects of the invention, it is helpful to understand the anatomical references of the body 50 with respect to which the position and operation of the device, and components thereof, are described. There are three anatomical planes generally used in anatomy to describe the human body and structure within the human body: the axial plane 52, the sagittal plane 54 and the coronal plane 56 (see FIG. 1B). Additionally, devices and the operation of devices are better understood with respect to the caudad 60 direction and/or the cephalad direction 62. Devices positioned within the body can be positioned dorsally 73, e.g., at a posterior side or end 70, such that the placement or operation of the device is toward the back or rear of the body. Alternatively, devices can be positioned ventrally 71, e.g., at an anterior side or end 72, such that the placement or operation of the device is toward the front of the body. Various embodiments of the device for isolating teeth, systems and kits of the present invention may be configurable and variable with respect to a single anatomical plane or with respect to two or more anatomic. Similarly, the various components can incorporate differing sizes and/or shapes in order to accommodate differing patient oral cavity sizes.

Provided herein is a retraction device for isolating the lower and upper arches of teeth located in the oral cavity. The retraction device can isolate the lower and upper arches of teeth. Additionally, the retraction device can isolate gum tissue located adjacent to the lower and upper arches. By isolating the dental surfaces, the device can be used to create a barrier that can efficiently separate the dental surfaces from any influence by saliva or other body fluids. A portion of the gum tissue can be isolated or the entire gum tissue can be isolated. The present invention contemplates devices adapted and configured to retract tissue in the oral cavity away from one or more dental arches or from one or more teeth. By retracting the tissue, teeth are set apart or kept away from other tissue, saliva, and debris to create a site within the oral cavity suitable to perform a dental procedure, such as dental imaging. As will be appreciated by those skilled in the art, because the teeth are embedded in the jaw bone, a target tooth is not per se "isolated" from a neighboring tooth. However, the devices, can be configured such that the target tooth is isolated from a neighboring tooth such that the neighboring tooth is not impacted by the use of dental materials during a procedure on the target tooth. Isolation of one or more target teeth can also include exposing those teeth to create a surgical sit, or site for performing a procedure. Isolation of one or more target teeth can also include creating a barrier that can efficiently separate dental surfaces from any influence by saliva or other body fluids.

The devices are further configured such that they are rapidly deployable. The devices are able to quickly achieve a dry working field and substantially maintain the working field condition during the procedure without the need for interaction. The device can isolate at least one arch of teeth in seconds. In some embodiments, the device can be deployed to isolate the upper and lower arches of teeth in less than about 60 seconds or 1 minute. In some embodiments, the device can be deployed to isolate the upper and lower arches of teeth in less than about 1 minute. In some embodiments, the device can be deployed to isolate the upper and lower arches of teeth in less than about 20 seconds.

In some embodiments, a device of the present invention is a single unit apparatus that can be positioned within a patient's mouth to isolate one or more of the patient's teeth by retracting tissue, including the tongue. The ability to retract the tongue provides considerable advantage for accessing the oral cavity. For example, a device can be a single arch that isolates only the upper teeth or a portion thereof or a single arch that isolates only the lower teeth or a portion thereof Such single-arch devices which isolate only lower or upper teeth can be used independently or in combination with one another to form a two piece device. In some embodiments, a single arch (e.g., lower arch) device is coupled to a paddle that isolates the other half of the mouth and tongue (e.g., the upper teeth) and/or keeps the mouth open. Since the device herein is shaped like the mouth, the device can be inserted into a patient's mouth accurately in about one minute or less or about 20 seconds or less.

The devices herein include one or more retractors. A retractor is an element that deflects, retracts, or displaces soft tissue, such as lips, tongue and/or cheek(s), away from teeth and/or alveolar surfaces. In some embodiments, a device comprises one retractor. In some embodiments, a device comprises two retractors. The tongue can be deflected by an open tongue retractor structure, such as a wire tongue retractor. Alternatively, the tongue retractor can include a cover for containing the tongue from the sides. The tongue can be entirely confined within the tongue retractor so that the tongue is confined within a restricted space and thereby prevented from filling the oral cavity. Additional retractors can be used, especially when each retractor uniquely retracts a different portion of the cheek(s) and/or lip(s).

Devices can further be adapted and configured to provide one or more apertures that correspond with one or more upper and/or lower teeth. A lower retractor may be provided adjacent an aperture for the lower teeth such that it is adapted and configured to extend or protrude the lower lip and cheeks away from the lower teeth, or at least a target lower tooth, e.g. where only one tooth is exposed through the lower tooth aperture. Similarly, an upper retractor may be positioned adjacent an aperture corresponding to one or more upper teeth, wherein the retractor is adapted and configured to extend or protrude the upper lip and cheeks away from the upper teeth, or at least a target upper tooth. The upper and/or lower teeth can be inserted into such tooth receiving apertures without impinging on the patient's teeth and without forceful contact with the alveolar process or gingiva. In some embodiments, additional regions of interest (e.g., gums) may be exposed by using a more minimal device or by removing (such as by cutting) one or more parts of the device as necessary.

The retractor can have various dimensions to achieve suitable to achieve creation of a working field around a target tooth or teeth. Thus, the length, height, curvature (including the radius of curvature), and width can be adjusted to take into account the size of the mouth and/or the facial features of the patient. For example, in some embodiments, retractors can be configured to increase in size as the retractor extends away from the alveolar arch to allow for retraction of more cheek muscle. In some embodiments, a lower retractor and/or an upper retractor is between about 1 mm to about 10 cm in height. Retractors for children, adults, and animals can have different lengths, widths, curvatures, including frame elements having varying radii of curvature, etc.

The lower and upper retractors can be adapted to extend to the back of the mouth where the retractors interconnect. For example, the lower and upper retractors may be connected on both the right and left back (posterior) sides of the mouth, e.g. immediately posterior the most posteriorly positioned tooth, via a flexible bridge that permits the patient to open and close their mouth with the device fully deployed therein. Such a bridge can include, for example, one or more features adapted to increase flexibility or rigidity. In some embodiments, the bridges comprise folds, bellows or ribs which increase its elasticity. In some devices, the bridges are made of a different material than the retractors. Additionally, the lower and upper retractors can be connected via an inflexible bridge forcing a patient to keep their mouth open at a specified angle. In some embodiments, the bridges are designed to help keep a patient's mouth open but also provide flexibility to permit closing of the mouth.

A flange or bridge (such as "webbing") can also be provided that connects the anterior portion of the lower retractor prevents the tongue from dislodging the device by positioning the tongue over the top of the webbed portion described.

The bridges in the back of the mouth can be coupled to or extend into a shield that prevents debris and other components from entering the throat during a dental procedure. The shield can have a proximal curvature to allow extra room for the tongue. In some embodiments, the shield curvature is such that the apex of curvature is in the center of the mouth. In some embodiments, the shield can further act as a tongue containment device, tongue retractor, tongue deflector, tongue suppressor, tongue elevator, tongue support, etc. In some embodiments, the shield comprises an aperture or apertures (mesh) in its center to permit a patient to breathe using their mouth. The aperture allows the patient to breath through the mouth. Additionally, the aperture may be large enough such that the patient can put their tongue into and/or through the aperture. The aperture can also be used to provide access to the back of the mouth e.g. to visualize debris or saliva build-up, as well as to give access to high volume suction.

Some configurations of the shield are configured to function as a tongue retractor comprises a surface that is a u-shaped flange extending from the inside of the mouth toward the outside. The bottom surface of the tongue retractor can have an internal surface with side surfaces extending from top to bottom forming a barrier between the mouth and the throat. The throat barrier is below the breathing aperture, which permits the patient to breathe through the mouth during the procedure.

In some embodiments, a shield can be used to maintain the patient's mouth in an open state. Such shield has a support mechanism above the breathing cavity. The support mechanism may be a u-shaped flange that extends upwardly and externally above the breathing cavity. The support mechanism is adapted to maintain the mouth cavity open. The support mechanism is especially useful for dental surgery, when the patient is unconscious or sedated.

Devices of the invention can also be adapted and configured to integrate with a saliva ejection or suction/evacuation element. A saliva suction element includes, for example, one or more suction inlets, one or more suction channels, and one or more suction outlets. A suction channel can extend from a region inside the mouth (e.g. posteriorly and then forward in and around the alveolar process under the tongue) to a region near or at the mouth opening (e.g. anteriorly). A suction channel can be integrated into the frame of the device. For example, a suction inlet can be at a region abutting the internal cheek or back of the mouth when the device is deployed. In some embodiment multiple suction inlets align the bottom lower retractors. Such suction inlets are coupled to a single channel leading to an outlet or port in the front of the patient's mouth. A suction channel can extend from the suction inlet within the frame of the device, or external to the device, to a suction outlet or port located at the proximal end of the device herein or proximal to the device herein (external to the mouth). The suction port can be coupled to a suction device external to the patient to draw saliva from the back of the mouth outside the patient. A saliva ejection or suction element enhances the seal around the teeth. In some embodiments, suction channels(s) and outlet(s) are located on the underside (meaning the "tissue side") of the "sealing mechanism" such that the device attaches itself firmly to the alveolar process or upper and lower alveolar processes when suction is applied. The suction actuated sealing mechanism can also consists of a suction channel within the "windshield wiper blade" or retractor element, with perforations positioned in two rows on the tissue side ("underside") of the seal. In the case of the upper arch portion of the device, the perforations are on the superior surface of the seal. When suction is applied to the channel or channels, via a port or ports near the proximal end of the device, the seal(s) adhere(s) to the alveolar process or processes. The suction is also capable of evacuating saliva on the tissue side of the barrier while evacuating debris and other contaminates on the working field side of the barrier.

The devices herein can also be integrated with a lighting element. As with other components of the invention, the integrated light can be formed integrally, such that it is a constituent piece of the device, or such that the device ultimately forms a single unit, one component of which is the light fixture. Such devices are composed of a translucent material capable of illuminating once it is inserted into the patient's mouth. In some embodiments, the device comprises LED light source or a fiber optic light source, or an effervescent light source either of which can, for example, be embedded in the device or coated on the device. The lighting device can also be configured such that it is powered by an external power source or a power source that is not external. Light sources can be located along the sides of the device, or along the top or the device or along the bottom of the device or all over the device.

The devices herein can be manufactured using an elastic but somewhat stiff wire to form the upper and lower retractors. The wire can be encapsulated in silicone and then encapsulated by a soft polymeric material, for example. In some embodiments, the wire is a polymer wire. Alternatively, the wire can be a metal wire. In some embodiments, the wire is used by itself without a soft membrane or coating. In some embodiments, a nickel/titanium alloy wire is used for the frame to optimize the collapsibility of the device for insertion purposes and compliance with mouth shape while providing the forces necessary to accomplish retraction of cheeks and tongue and to position the sealing mechanism. The heat in the oral cavity can activate property changes in the metal springing it into its designed shape making it less intrusive to insert. In some embodiments, a nylon or other plastic material is used for this "wire frame" that may be effected by the body heat also.

The devices described herein are particularly useful in aiding the imaging or scanning of the dental surfaces located within the oral cavity. The device can be used to create a larger working field, wherein the working field comprises the dental surfaces of interest and the area surrounding the dental surfaces of interest. The devices described herein can be used to create a larger working field to facilitate imaging the oral cavity. The oral cavity can be imaged using radiology equipment, such as X-rays, or to scan the dental surfaces by enabling a better insertion of the scanning device into the oral cavity. Additionally, the larger working field, together with the dry dental surfaces created by the devices, further facilitate the scanning of the dental surfaces by allowing for the placement of a powder on the dental surfaces, wherein the power aids in the ability to scan the dental surfaces. The devices can also be used to facilitate the generation of dental impressions by ensuring proper placement of dental trays within in the oral cavity since the devices can embody a design with minimal material, thereby taking up less space in the oral cavity. This provides for less interference by both the devices and the soft tissue with the materials and kits needed to create the dental tray. The ability to make a dental impression, utilizing the established, well controlled, full arch working field provided by the device provides a major advantage to the dentist. The dentist can transition directly from procedures involving the teeth or periodontal structures to making an impression of the area or an entire arch of teeth without removing the device or ever compromising the working field required for a complete and accurate impression.

The remainder of the devices herein can be made from one or more polymeric materials including, but not limited, to c-Flex-thermal plastic elastomer (TPE), silicon, slow recovery foam (SRF), and polypropylene (PP). Preferably, a clear polymer is used to manufacture the devices herein. The material can be embossed or pre-molded into the shape of the inside of the mouth which provides extra comfort to the patient. The device can be composed of one or more materials or of a single material having two or more durometers. In one embodiment, a first material conforms to the shape of the alveolar process(es) and creates a seal around one or more of the teeth while the second material provides a structure that retracts the cheek(s) and tongue, providing a clear working field for the dental practitioner and comfort and safety for the patient. In any of the embodiments herein, a material can optionally contain a lubricant or flavored lubricant to facilitate insertion and removal. In some embodiments, the device is molded in the practitioner's office to fit the individual patient. In some embodiments, a practitioner can measure a patient's mouth, using a sterilizable and reusable "tri-in" device, as an aid in selecting the best size of device for the patient. Overall, the device herein can be made in different sizes to fit different size mouths. In some embodiments, a device herein can be used in veterinary dental procedures. Such devices can be adapted to fit an animal being treated (e.g., dog, cat, horse, etc.). The sealing portion of the device can be formed from any suitable hydrophilic material, hydrophobic material, or a putty (e.g., Van-R reversible hydrocolloid, available from Dux Dental, and vinyl polysiloxane, available from 3M Express).

Prior to inserting the devices described herein into a patient's mouth, the devices have a circular circumference as provided by the upper and lower retractors. The devices can have at least one, two, or three apertures—e.g., one for one or more of the lower teeth, and/or one for one or more of the upper teeth, and/or one for the tongue and/or airway and/or the largest (proximal or posteriorly positioned) aperture which is used for access to the working field. The apertures for the target teeth (either upper or lower) can be formed by implanting the device and punching one or more target teeth through a perforated ridge. In some embodiments, a first aperture is designed to expose/isolate all of the target teeth and is c-shaped; a second aperture is designed to expose/isolate all of the target teeth. The first and second apertures border on their exterior end with retractors adapted to retract the lips and cheeks away from all teeth. The upper and lower retractors are coupled in the back of the mouth using flexible bridges that permit the patient to open their mouth at various angles. The bridges are also coupled to a shield with an aperture large enough to allow at least a portion of the patient's tongue to protrude through it.

As will be appreciated by those skilled in the art, the devices can be adapted and configured to completely isolate both full arches of teeth and is adapted to permit closing of the mouth. This may allow the upper and lower teeth to come together and permits a dental practitioner to make a judgment about the interaction(s) of upper and lower teeth (e.g., bite). The ability to look at all arch of teeth also permits judgment based on features of other teeth whether they are being worked on or not (e.g., comparing teeth coloration, etc.). Furthermore, exposing a plurality of teeth permits a dental practitioner to work on more than 1, 2, 3, 4, 5, 6 etc., teeth each of which may be located in a different part of the mouth without having to re-adjust the device.

The devices are adapted and configured for use in a procedure requiring a dry environment, such as performing restoration (e.g., crown and filling work) or creating molds of the oral cavity. Absence of saliva can impact the quality of a tooth impression, especially when making impressions of teeth prepared for laboratory fabricated dental restorations or prostheses. The devices of this invention enable a practitioner to insert the device, optionally perform suction on any saliva that remains in the patient's mouth or perform any other step to facilitate a dry working field, and then insert impression material onto a tooth, remove that impression material and optionally insert a filling material. The devices permit an impression to be taken and filling added without removing the device so that no impression or filling material goes down the patient's throat. The devices also helps prevent saliva from getting onto the teeth during the entire period it is placed in the mouth.

For surgical procedures, the devices can be used to isolate one or more teeth of interest while preventing blood, disposables, implantable parts, implanted related parts, or instruments from getting into the patient's throat. The device can be used to create a barrier that can efficiently prevent inhalation or ingestion of The retraction devices described herein can comprise a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity. In some embodiments, the conformable structure is a frame. Additionally, the frame can further comprise a membrane. The frame can also comprise a light source. The device can be adaptable to be deployed in under 1 minute. In some embodiments, the device can be adaptable to create a working field in under 1 minute. The device can be deployed in under 20 seconds. The device can further comprise a tongue retractor wherein the tongue retractor can be adaptable to deflect the tongue without passing over either arch of teeth. The tongue retractor can contain and confine the tongue in a restricted space.

In some embodiments, the device can further comprise at least one evacuation element. The device can be adaptable to retract soft tissue surrounding at least one arch of teeth. Additionally, the device can be adaptable to retract the upper and lower arches of teeth in the oral cavity. The device can also be used in some cases to isolate at least a portion of gum tissue in the oral cavity. Furthermore, the device can comprise at least one aperture to facilitate the ability to breathe through the device. The device can facilitate the scanning of the dental surfaces wherein the scanning comprises at least one of digital scanning or optical scanning. Furthermore, the device can be adaptable to isolate both arches of teeth is less than 20 seconds. In some embodiments, the device can be adaptable to be positioned without interfering with access to dental surfaces and further adaptable to provide maximum patient comfort.

Further provided herein is a retraction device comprising a topology conformable structure adaptable to create a working field in an oral cavity of a patient, wherein the working field is at least 10% larger than a working field created in the oral cavity of the patient without use of the device. The device can be used to provide at least 10% more access to an area of interest in the oral cavity. In some embodiments, the area of interest is one arch of teeth. Alternatively, the area of interest can be both arches of teeth. The device can be adaptable to provide at least 10% more visibility within the oral cavity. The device can be adaptable to provide at least 10% less contamination of structures located in the oral cavity by fluid. The fluid can be saliva, blood, or any other bodily fluid. In some embodiments, the device can be adaptable to provide at least 10% less interference between soft tissue and instruments accessing the oral cavity. The conformable structure can be a frame. In some embodiments, the frame is a wire frame. In some embodiments, the device further comprises a membrane. Additionally, the device can comprise a light source. The device can be adaptable to isolate at least one arch located within the oral cavity. The device can be adaptable to isolate the upper arch and the lower arch in the oral cavity. In some embodiments, the device can be adaptable to isolate at least a portion of gum tissue in the oral cavity. The device can be used to isolate the entire gum tissue. Furthermore, the device can be adaptable to be deployed in under 1 minute. The device can also be adaptable to create a working field in under 1 minute. In some embodiments, the device can be deployed in under 20 seconds. Additionally, no further adjustment of the device can be needed after the device has been deployed. In some embodiments, the device can further comprise a tongue retractor. The tongue retractor can contain and confine the tongue in a restricted space. The tongue retractor can be adaptable to allow a first occlusal surface and a second occlusal surface to touch. The tongue retractor can be adaptable to compress at least one side of the tongue or both sides of the tongue. The device can be adaptable to apply suction to the oral cavity. The device can be used to evacuate the oral cavity. The device can be adaptable to apply suction to the oral cavity through at least one aperture adaptable to facilitate the ability to breathe through the device. The device can be adaptable to isolate at least one dental arch in less than 20 seconds. The device can further be adaptable to be positioned without interfering with access to dental surfaces and further adaptable to provide maximum patient comfort.

Additionally, provided herein is a retraction device comprising a malleable frame adaptable to be in a constrained shape that can be delivered into an oral cavity and further adaptable to be in an unconstrained shape to isolate at least one arch of teeth from saliva and soft tissue surrounding the arch. The malleable frame can be a wire frame. The malleable frame can further comprise a membrane. Additionally, the device can further comprise a light source. In some embodiments, the device can be adaptable to be deployed in under 1 minute. The device can be adaptable to be deployed in under 20 seconds, in some embodiments. The device can also be adaptable to create a working field in under 1 minute. Furthermore, the device can comprise a tongue retractor. The tongue retractor can contain and confine the tongue. The tongue retractor can be adaptable to allow a first occlusal surface and a second occlusal surface to touch. The device can also comprise at least one evacuation element. The device can be adaptable to retract soft tissue surrounding at least one arch of teeth or in some cases, retract the soft tissue surrounding the upper and lower arches of teeth. The device can be adaptable to isolate at least a portion of gum tissue located in the oral cavity. In some embodiments, the device further comprises at least one aperture to facilitate the ability to breathe through the device. The device can be further adaptable to facilitate the application of a substance to at least one tooth surface. The substance can be a powder. In some embodiments, the power is a reflective powder. The powder can help create a pattering on the surface the teeth. The device can also be adaptable to isolate at least one dental arch in less than 20 seconds. The device can be adaptable to create a working field without interfering with access to dental surfaces. The device can be further adaptable to be positioned in the mouth to provide for maximum patient comfort.

Figure 1B:
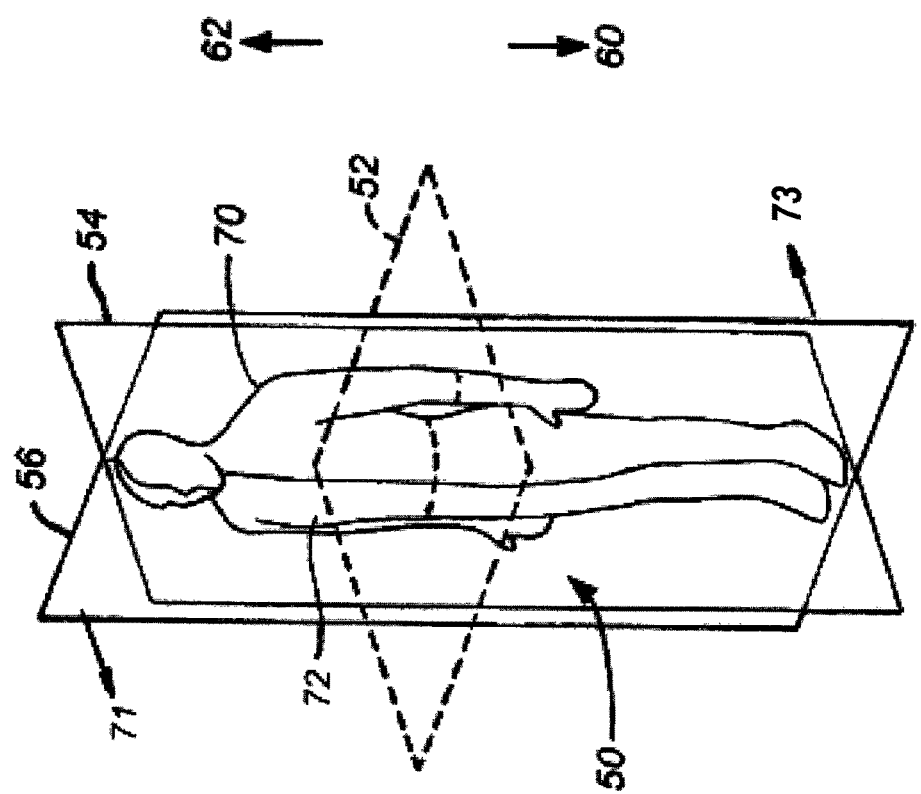
FIG. 1B is an illustration of a human body with the anatomical planes of the body identified.

As described above, FIG. 1A depicts an oral cavity 10 from an anterior 72 view with the mouth 10 open and the teeth exposed 20 and FIG. 1B illustrates a human body with the anatomical planes of the body identified.

I. Devices

Figure 2A:
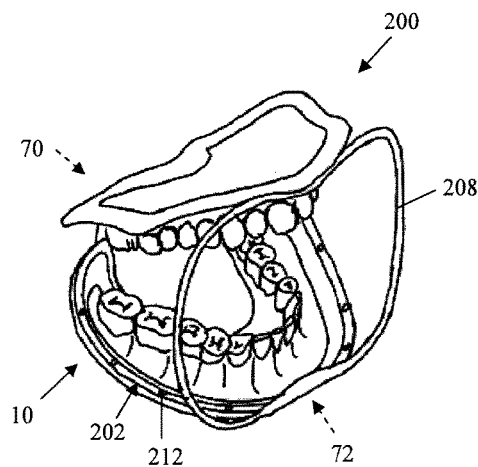
FIGS. 2A-2E illustrate one embodiment of a retraction device positioned in the oral cavity of a patient.
Figure 2B:
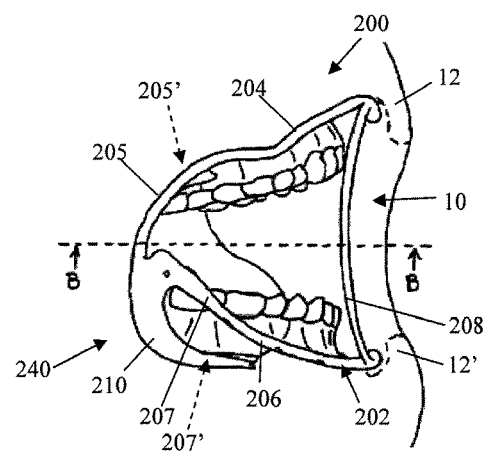
Figure 2C:
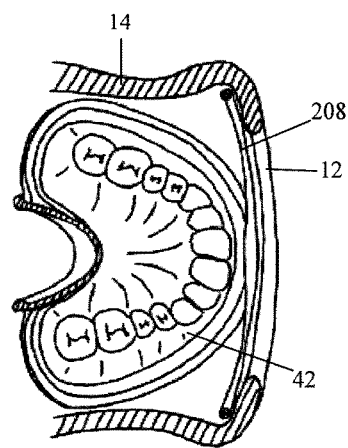
Figure 2D:
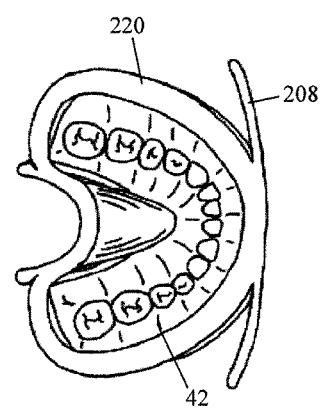
Figure 2E:
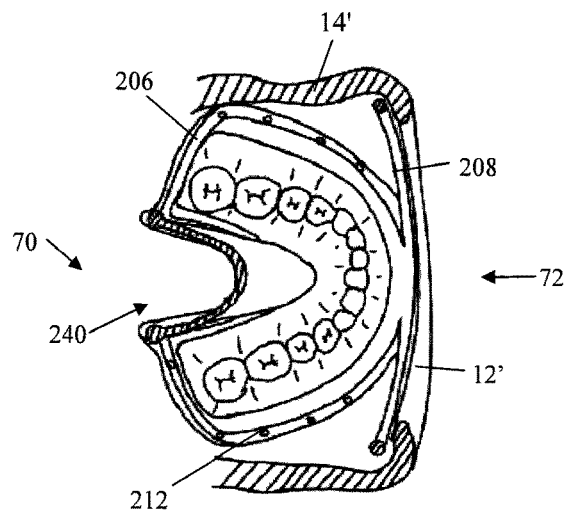
Figure 2F:
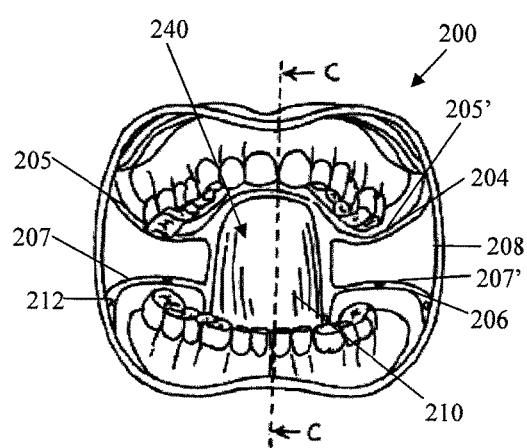
FIG. 2F depicts an anterior view of the device positioned in the oral cavity.
Figure 2G:
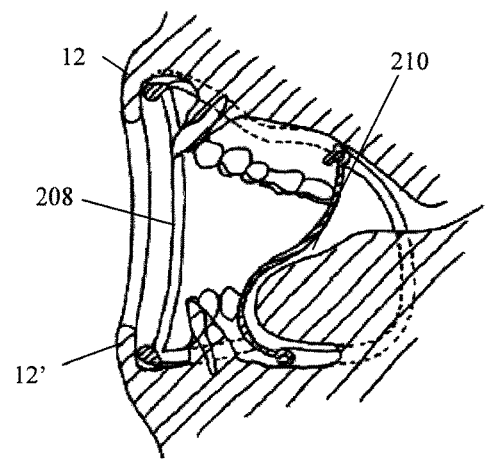
FIG. 2G depicts a cross-sectional view of the device, and surrounding tissue structures, along the sagittal plane.

FIG. 2A illustrates a perspective view of one embodiment of a retraction device 200, as viewed from the front and at an above angle as positioned within the oral cavity 10. The device 200 can comprise a cheek or soft tissue retraction frame 202 having an anterior end 72 and a posterior end 70. The device can further comprise a lip ring 208 for retracting at least one lip. Additionally, the device can comprise an evacuation component capable of suctioning fluid from the oral cavity. The evacuation component can be in communication, preferably fluid communication, with the oral cavity 10 through at least one inlet 212 in the frame 202. FIG. 2B is a side view of the device 200 as positioned within the oral cavity 10. The frame can be comprised of an upper frame 204 having a first end 205 and a second end 205' and a lower frame 206 having a first end 207 and a second end 207', and wherein respective first ends 205, 207 and second ends 205', 207' are connected via a cross member 240. In some embodiments, inlets 212 for evacuating the oral cavity 10 can be located in the upper frame 204 and the lower frame 202. FIG. 2B also illustrates how the lip ring 208 can be used to retract the lips 12, 12'. In some embodiments, the device can further comprise a tongue retractor 210 having an elongated structure with an upper end and a lower end when viewed from a sagital plane perspective, a curved shape when viewed from a coronal plane perspective, and a surface between said upper and lower ends to limit forward movement of a tongue toward a patient's teeth. FIG. 2C illustrates a cross-sectional view of the oral cavity along the line B-B in FIG. 2B. FIG. 2C is a cross sectional view of the caudal side of the oral cavity. FIG. 2C illustrates the positioning of the upper frame 204 of the device 200 around the gums of the upper dental arch 42, retracting the cheek tissue 14 away from the gums. FIG. 2C also illustrates how the upper portion of the lip ring 208 can retract the upper lip 12. FIG. 2D illustrates the complete frame viewed from the top of the device in position around the upper dental arch and the upper portion of the lip ring 208 without any surrounding soft tissue. The gum protection cover 220 is covering the upper frame in FIG. 2D. FIG. 2E illustrates a cross-sectional view of the oral cavity along the line B-B in FIG. 2B, viewing the cephalic portion of the oral cavity. FIG. 2E illustrates how the lower frame 206 of the device isolates the gums of the lower dental arch from the cheeks tissue 14'. FIG. 2E also illustrates the retraction of the lower lip 12' by the lip ring 208. FIG. 2E also shows inlets 212 in the frame for evacuating fluid from the oral cavity. FIG. 2F illustrates a frontal view of the device 200 in position in the oral cavity 10. FIG. 2F illustrates the upper frame 204 and the lower frame 206 and a lip ring 208. The lower frame 206 has inlets 212 for providing suction. FIG. 2F also illustrates a device 200 with a tongue retractor 210 as viewed from the front. FIG. 2G illustrates a cross-sectional view of the device 200 shown in FIG. 2G along the line C-C.

Figure 3A:
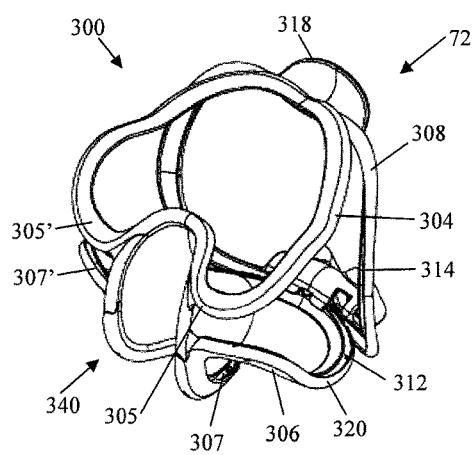
FIGS. 3A-3D illustrate one embodiment of a retraction device.
Figure 3B:
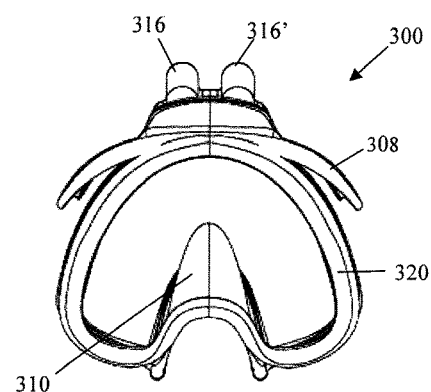
Figure 3C:
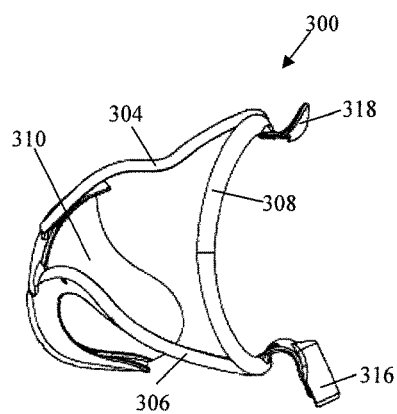
Figure 3D:
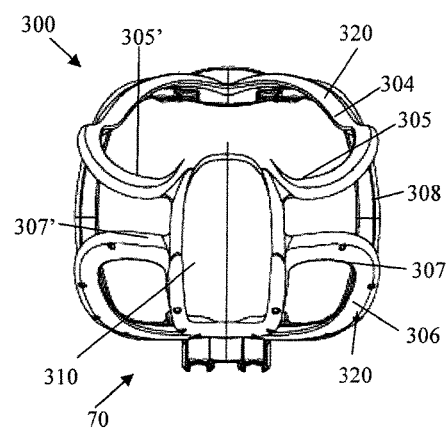

FIGS. 3A-3D illustrates one embodiment of an isolated retraction device. FIG. 3A illustrates a perspective view of the device as viewed from the distal end of the device 300, wherein the device has an anterior end 72 and a posterior end 70 positionable distally in the oral cavity. FIG. 3A illustrates an upper frame 304 having a first end 305 and a second end 305', a lower frame 306 having a first end 307 and a second end 307', wherein respective first ends 305, 307 and second ends 305', 307' are connected via a cross member 340, and a lip ring 308. The lower frame comprises inlets 312 for evacuating the oral cavity. FIG. 3A also illustrates a device 300 comprising a lip ring 308 further comprising a light ring 314. The device in FIG. 3A also comprises a tongue retractor 310 having an elongated structure with an upper end and a lower end when viewed from a sagital plane perspective, a curved shape when viewed from a coronal plane perspective, and a surface between said upper and lower ends to limit forward movement of a tongue toward a patient's teeth. FIG. 3B is a top view of the retraction device 300. FIG. 3B illustrates the upper frame with gum protection cover 320, the top portion of the lip ring 308, and the light sources 316, 316' for providing light to the light ring portion of the lip ring 308. The light source can either be isolated power sources for light, such as self-contained batteries, or alternatively, the light sources can be connectors which can be used to plug in an external power source. The light ring can be used to illuminate the oral cavity. The light ring can comprise any suitable feature for generating light to illuminate the oral cavity including, but not limited to, light emitting diodes (LEDs), fiber optic wires, light bulbs, fluorescent or chemiluminescent light sources, or any other suitable light source. The light sources 316, 316' can be connected to an external power supply. Alternatively, the light sources can comprise batteries. FIG. 3C illustrates a side view of the isolated retraction device 300. In addition to the upper frame 304, the lower frame 306, the tongue retractor 310, lip ring 308, light ring 314, and light sources 316, the device 300 can further comprise a lip rest 318 for providing further retraction of the lip and to facilitate placement of the device. FIG. 3D illustrates a posterior view of the device 300 illustrating the upper frame 304 with gum protection cover 320, the lower frame 306 with gum protection cover 320, portions of the lip ring 308, and the posterior side of the tongue retractor 310.

Figure 4A:
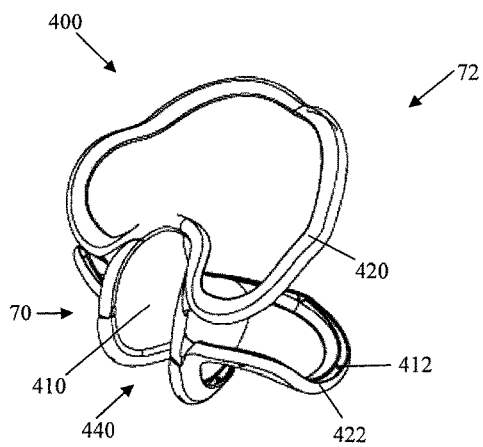
FIGS. 4A-4D illustrate the tongue and gum protection cover isolated from the retraction device.
Figure 4B:
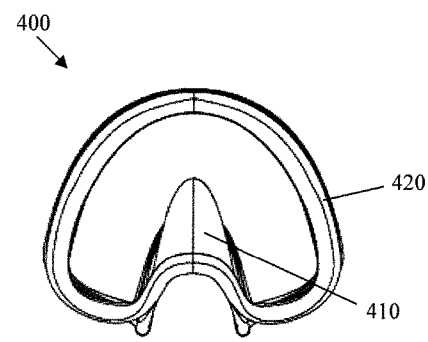
Figure 4C:
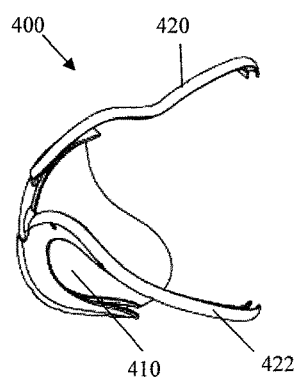
Figure 4D:
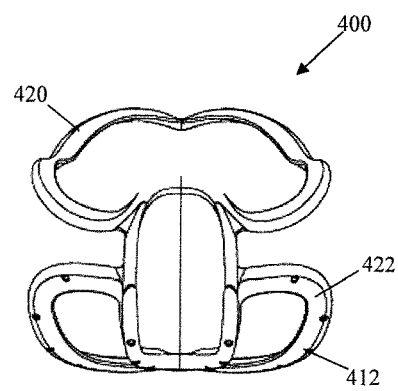

FIGS. 4A-4D illustrate the upper gum protection cover 420 and the lower gum protection cover 422 isolated from the retraction device, wherein the device has an anterior end 72, a posterior end 70, and a cross member 440. FIG. 4A is a perspective view of the gum protection covers 420, 422, and the tongue retractor 410 having an elongated structure with an upper end and a lower end when viewed from a sagital plane perspective, a curved shape when viewed from a coronal plane perspective, and a surface between said upper and lower ends to limit forward movement of a tongue toward a patient's teeth. Inlet 412 can be seen in the lower gum protection cover 422. The inlets 412 can provide communication, preferably fluid communication, between the oral cavity and the retraction device. The upper and lower gum protection covers can be rigid. Alternatively, the gum protectors can be soft, pliable membranes. The gum protectors can be made out any suitable material including, but not limited to, rubber, wax, foam, or any other suitable material or combination thereof FIG. 4B is a top view of a retraction device 400, illustrating the upper gum protector 420 and the tongue retractor 410. FIG. 4C illustrates a side view of the gum protection covers, both the upper gum protection cover 420 and the lower gum protection cover 422. FIG. 4C also shows the tongue retractor 410. FIG. 4D illustrates a posterior view of the retraction device 400, illustrating the upper gum protection cover 420 and the lower gum protection cover 422. Inlets 412 for evacuating the oral cavity can be seen in the lower gum protection cover 422.

Figure 5A:
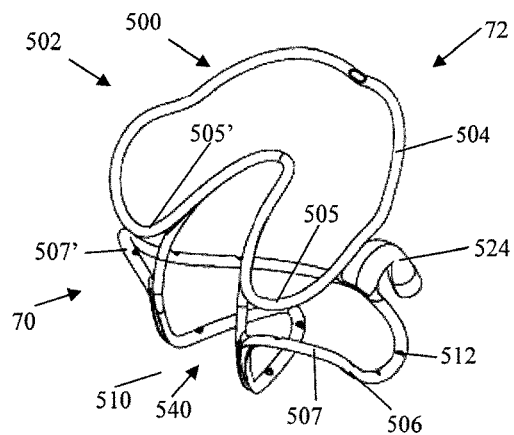
FIGS. 5A-5D illustrate the frame covering both the upper and lower arches of the retraction device, isolated from the membrane of the retraction device.
Figure 5B:
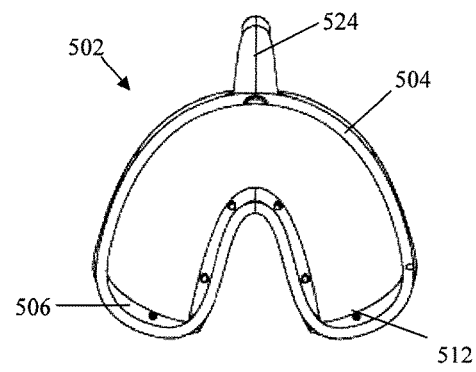
Figure 5C:
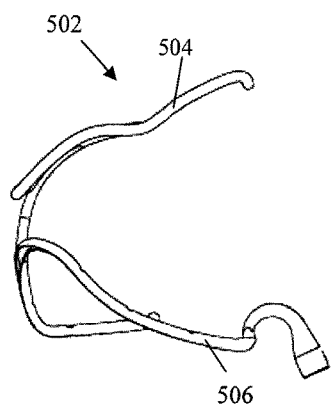
Figure 5D:
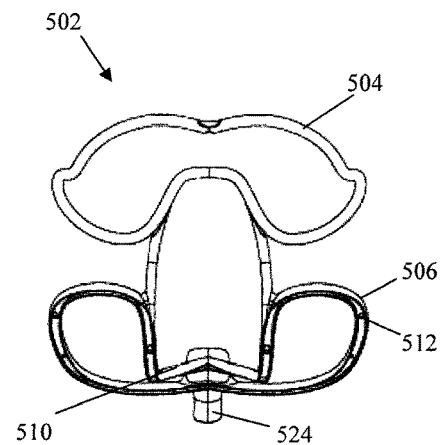

In some embodiments, the retraction device 500 is comprised of a frame 502, as shown in FIGS. 5A-5D. The frame 502 can be further comprised of an upper frame 504 having a first end 505 and a second end 505' and a lower frame 506 having a first end 507 and a second end 507', wherein respective first ends 505, 507 and second ends 505', 507' are connected via a cross member 540. The frame can be a malleable frame. It can be shaped to conform to the topology of the patient's oral cavity. In some embodiments, the frame is a wire frame. In some embodiments, the frame is made of a moldable plastic or wax. The frame can be made out of any suitable material for making the frame. Inlets 512 for evacuating the oral cavity can be seen in the lower frame 506. A suction port located on the bottom frame 524 can be used to introduce suction through the inlets 512 in the lower frame 506. FIG. 5A also illustrates a tongue retractor 510 having an elongated structure with an upper end and a lower end when viewed from a sagital plane perspective, a curved shape when viewed from a coronal plane perspective, and a surface between said upper and lower ends to limit forward movement of a tongue toward a patient's teeth. FIG. 5B is a view of the retraction device 500 from the top showing the top frame 504, the bottom frame 506, inlets 512 in the bottom frame, and the tongue retractor 510. FIG. 5C illustrates a side view of the frame 502, illustrating the top and bottom frames, 504, 506, respectively, and a tongue retractor 510. FIG. 5D illustrates a posterior view of the frame 502, showing the top frame 504, the bottom frame 506, and inlets 512 in the bottom frame 506.

FIGS. 6A-6D illustrate a light ring 614 isolated from the retraction device. The lip ring can be used to retract the cheeks, and lips. FIG. 6A illustrates a posterior perspective view of the light ring. The light ring 614 can have at least one light source 616, 616'. In some embodiments, the light ring can be a single unit with the lip ring. Alternatively, the light ring can be attached to the lip ring if necessary and may have two halves connected by a connector 626. The light ring 614 can have at least one opening 625 through which the oral cavity can be illuminated. FIG. 6B is a top view of the light ring 614, showing the light sources 616, 616'. FIG. 6C is a side view of the lip ring 614 showing the lip rest 618 and the light source 616. FIG. 6D is a posterior view of the light ring 614. FIG. 6D also shows a lip rest 618, openings 625, 625' in the lip ring for illuminating the oral cavity, and light sources 616, 616'.

Figure 7A:
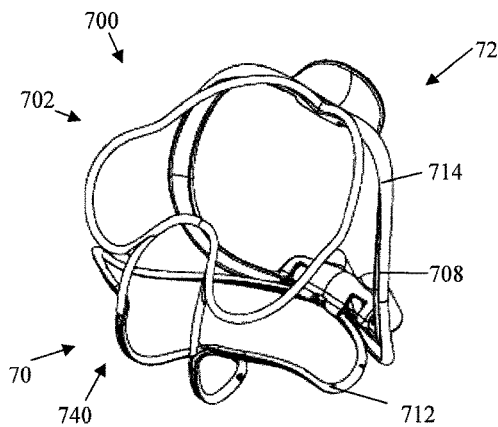
FIGS. 7A-7D illustrate an alternative embodiment of a retraction device without a tongue or gum protection component.
Figure 7B:
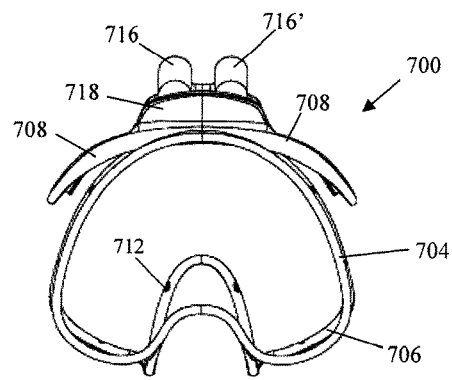
Figure 7C:
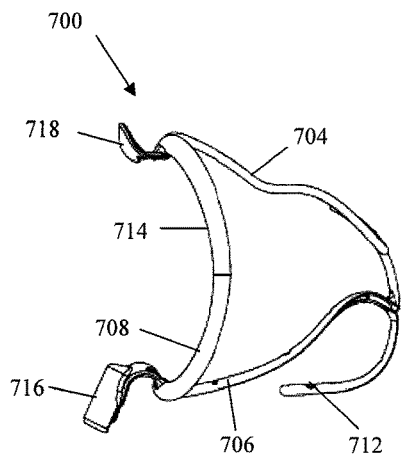
Figure 7D:
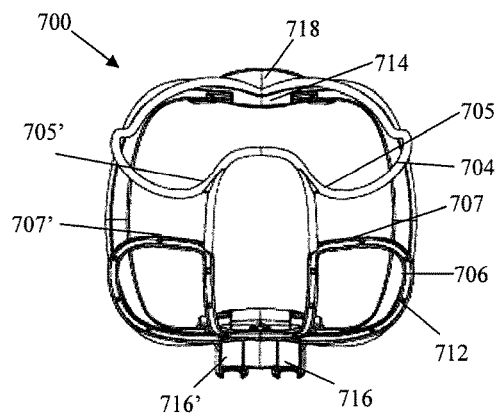

FIGS. 7A-7D illustrate an alternative embodiment of a retraction device 700, wherein the retraction device does not comprise a tongue retractor or gum protection covers. FIG. 7A illustrates a perspective view of a minimalistic retraction device 700 having an anterior end 72 and a posterior end 70 and comprising a frame 702, a lip ring 708 with a light ring 714. FIG. 7B is a top view of the retraction device 700 illustrating an upper frame 704 having a first end 705 and a second end 705', a lower frame 706 having a first end 707, a second end 707' and comprising at least one inlet 712 for evacuating the oral cavity, wherein respective first ends 705, 707 and second ends 705', 707' are connected via a cross member 740. The device can comprise more than one inlet. FIG. 7B also illustrates a top view of the lip ring 708 with a light ring 714, lip rest 718, and light sources 716, 716'. FIG. 7C is a side view of the retraction device 700 illustrating the upper frame 704, lower frame 706 with at least one inlet 712, lip ring 708, light ring 714 with lip rest 718, and light source 716. FIG. 7D is a posterior view of the retraction device 700.

Figure 8A:
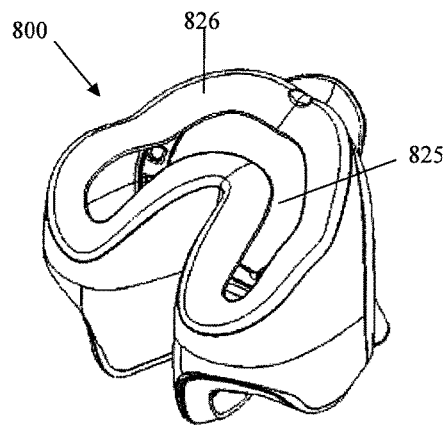
FIGS. 8A-8D illustrate an alternative embodiments of a retraction device having a frame covered by a membrane.
Figure 8B:
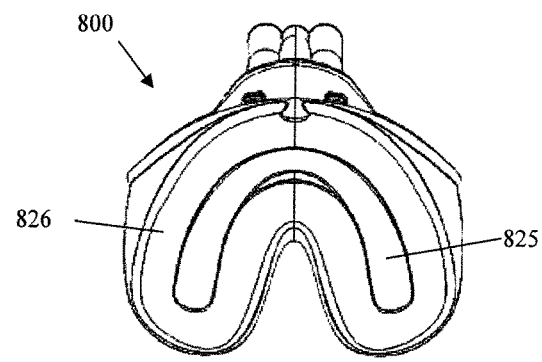
Figure 8C:
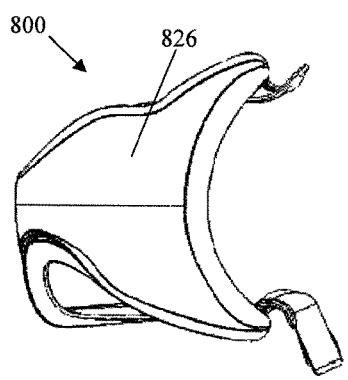
Figure 8D:
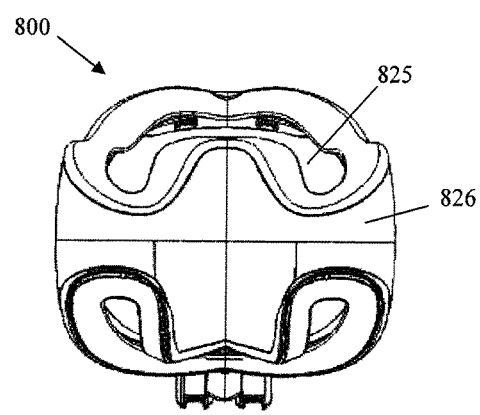
Figure 9A:
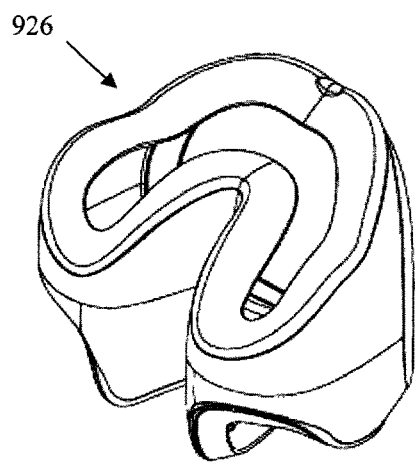
FIGS. 9A-9D illustrate the isolation membrane or cover of the retraction device isolated from the retraction device.
Figure 9B:
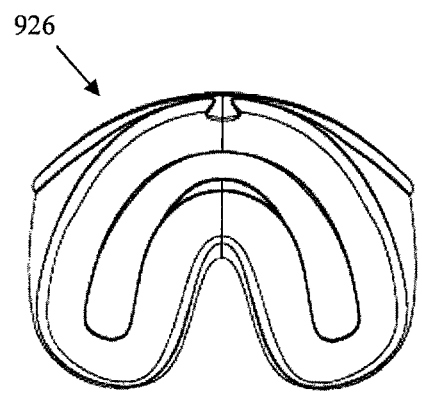
Figure 9C:
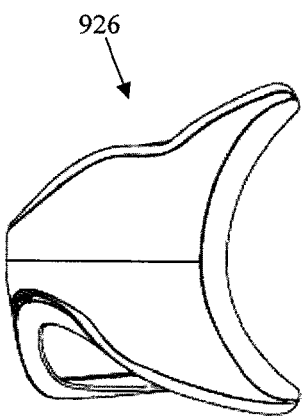
Figure 9D:
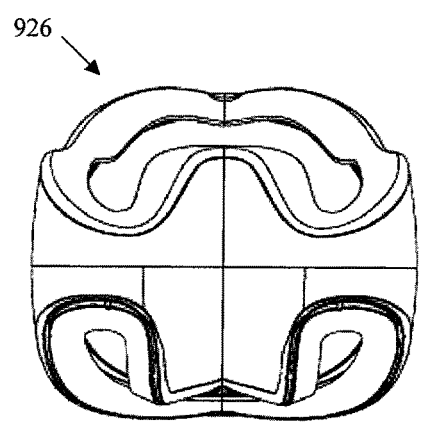
Figure 11A:
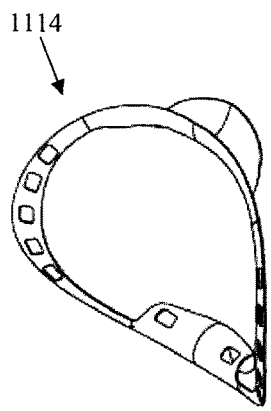
FIGS. 11A-11D illustrate an alternate embodiment of a light ring comprising a flexible electrical circuit membrane.
Figure 11B:
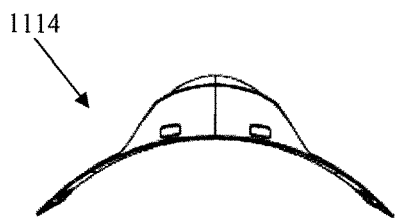
Figure 11C:
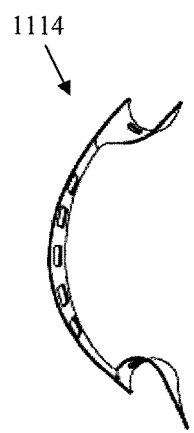
Figure 11D:
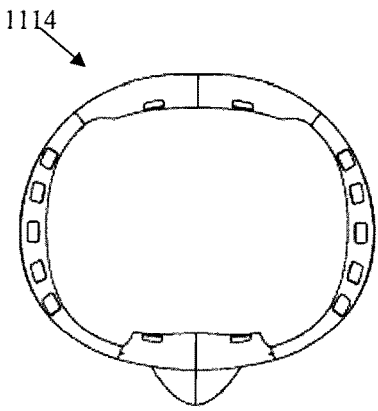

FIGS. 8A-8D illustrate an alternative embodiment of a retraction device 800 in which the frame is covered by a cover 826. The frame cover 826 can be a soft membrane material. The frame cover can be made of any suitable material including, but not limited to, rubber, or corn polymers, or "green" or environmentally friendly sustainable materials, or any of the materials previously mentioned. FIG. 8A is a perspective view of the device 800 with a cover 826 covering the entire device. In some embodiments, the cover can cover a portion of the device. The cover can have openings 825 which can fit around the dental surfaces in the oral cavity of the patient. In some embodiments, the opening 825 is a slit. In some embodiments, the opening has a shape similar to the dental arch. FIG. 8B illustrates a top view of the device 800 showing the cover 826 and an opening 825 in the cover 826. FIG. 8C is a side view of the device 800. The cover can cover the upper and lower frames of the device, with the space between the upper and lower frames remaining uncovered. Alternatively, the cover can cover the space in between the upper and lower frames as shown in FIG. 8C. FIG. 8D is a posterior view of the device.

FIGS. 9A-9D illustrate a cover 926 isolated from the retraction device. FIGS. 9A-9D show an isolated cover 926 for both the upper and lower frames.

FIGS. 10A-10D illustrate a light ring 1014 isolated from the retraction device. FIG. 10A illustrates a front perspective view of an isolated light ring 1014 illustrating the light sources 1016, 1016' and the outputs 1015 from the light ring 1014 which can be used to illuminate the oral cavity. The light ring 1014 can also have a lip rest 1018 as shown in FIG. 10A. FIG. 10B is a top view of the light ring 1014. FIG. 10C is a side view of the light ring 1014. FIG. 10D is a posterior view of the light ring 1014. The outputs 1015 from the light ring 1014 can be located in the upper part of the light ring, the lower part of the light ring, and on the sides of the light ring, as shown in FIG. 10D. Alternatively, the outputs 1015 from the light ring 1014 can be located in only the upper portion of the light ring. The light outputs can be located only in the lower portion of the light ring. The light outputs can be located in the sides of the light ring. The light outputs can be grouped together or the light outputs can be uniformly spaced throughout the light ring. The light outputs can be any suitable output for illuminating the oral cavity including, but not limited to, light bulbs, LEDs, fiber optics, or any combination thereof or any other suitable light output.

FIGS. 11A-11D illustrate an alternate form of a light ring 1114. In some embodiments, the light ring can be made of a flexible material, as shown in FIGS. 11A-11D. The flexible material allows the light ring to be flexed without damage to the circuit.

Figure 12A:
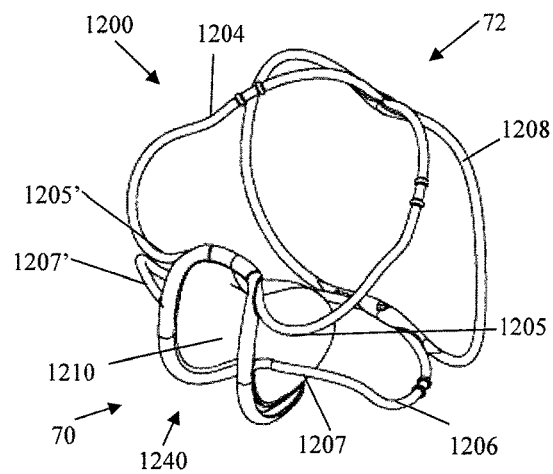
FIGS. 12A-12D illustrate an alternate embodiment of an isolated frame of a retraction device, including tongue cover, and lip and cheek retraction ring.
Figure 12B:
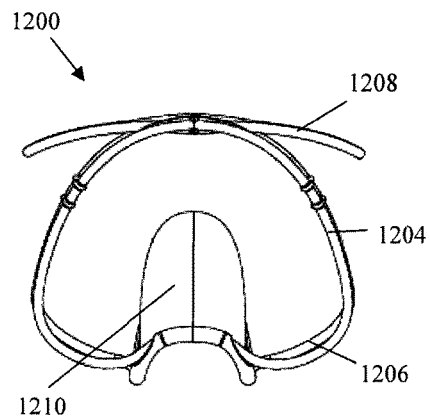
Figure 12C:
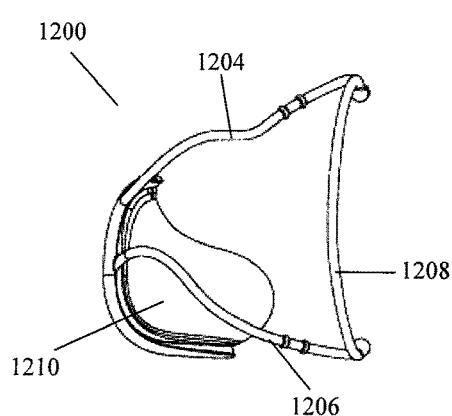
Figure 12D:
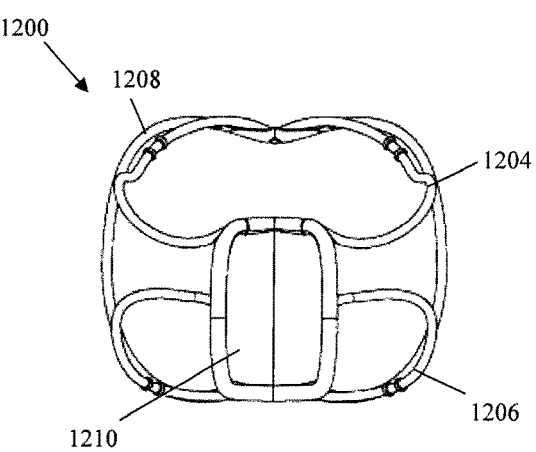
Figure 13A:
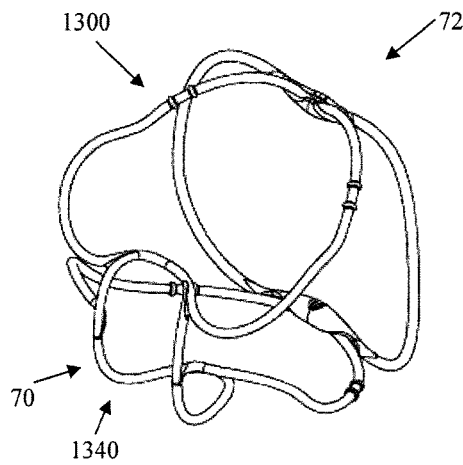
FIGS. 13A-13D illustrate an alternate embodiment of an isolated frame of a retraction device.
Figure 13B:
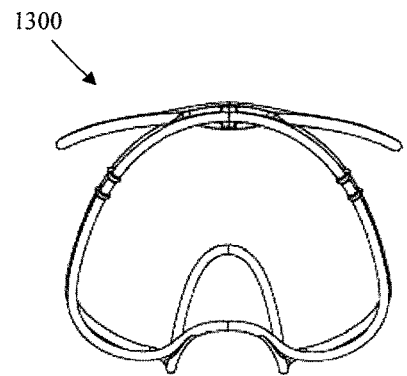
Figure 13C:
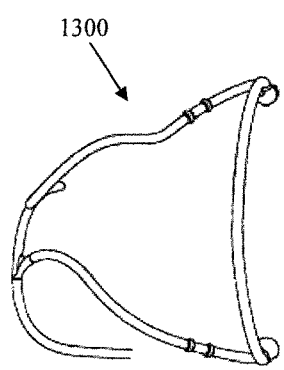
Figure 13D:
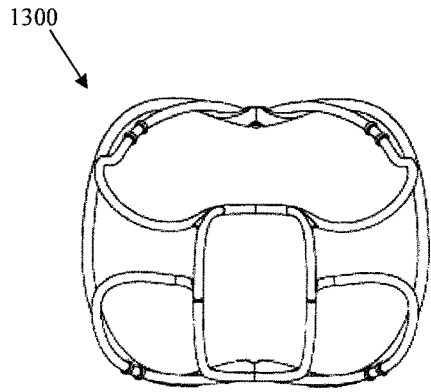

FIGS. 12A-12D illustrate an alternate embodiment of an isolated frame of the retraction device 1200 having an anterior end 72, a posterior end 70, and a cross member 1240. The frame design of the invention can provide better access to the palette area for scanning, as previously described. The upper and lower frames also facilitate insertion of a scanning device along the side of the frame. The tissue can be kept away from the teeth so that a powder coating can be applied to the dental surfaces. The mouth can be scanned in its entirety without stopping. FIG. 12A is a perspective view of the device as viewed from the posterior side of the device 1200. The lip ring 1208, the upper and lower frames, 1204, 1206 each having first ends 1205, 1205' and second ends 1207, 1207', respectively, and tongue retractor 1210 can be seen. FIG. 12B is a top view of the device 1200. FIG. 12C is a side view of the device 1200. FIG. 12D is a posterior view of the device 1200.

FIGS. 13A-13D illustrate an alternate embodiment of a retraction device 1300 without a tongue retractor and having an anterior end 72, a posterior end 70, and a cross member 1340.

FIGS. 14A-14D illustrate a frame 1402 isolated from a retraction device and having an anterior end 72, a posterior end 70, and a cross member 1440. The frame can be used alone to retract soft tissue. Alternatively, the frame 1402 can be used with other features or components, such as a soft cover for the frame, a light ring, or lip ring. FIG. 14A is perspective view of the frame 1402. FIG. 14B is a top view of the frame 1402. FIG. 14C is a side view of the frame 1402. FIG. 14D is a view of the posterior side of the frame 1402.

Figure 15A:
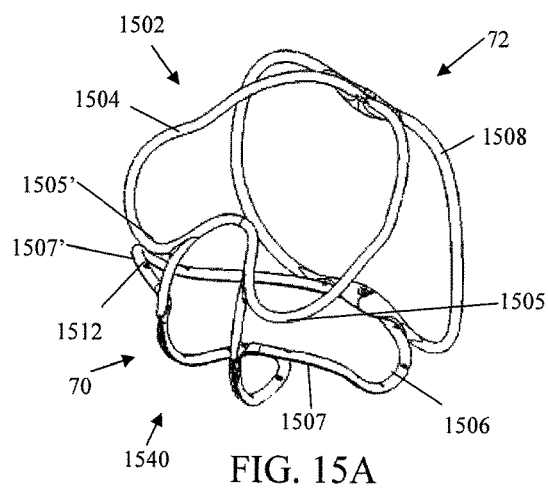
FIGS. 15A-15D illustrate an alternate embodiment of a frame comprising an evacuation component.
Figure 15B:
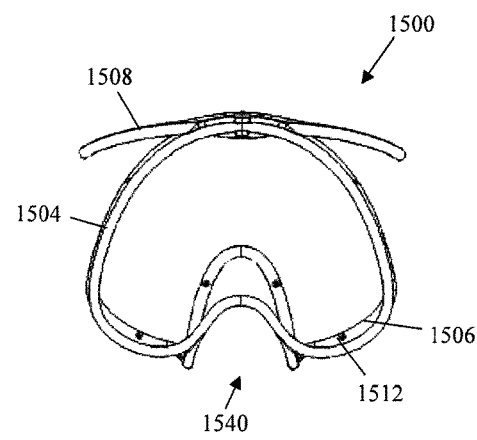
Figure 15C:
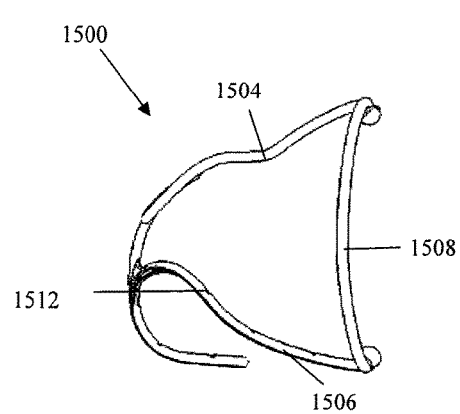
Figure 15D:
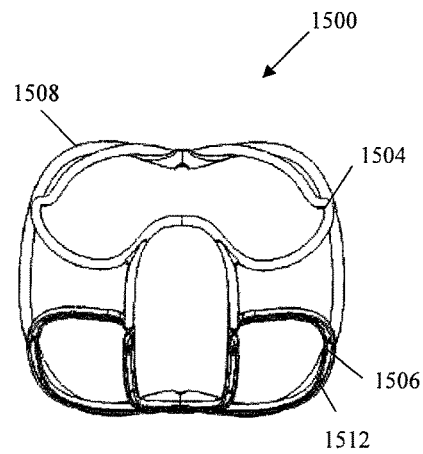
Figure 19A:
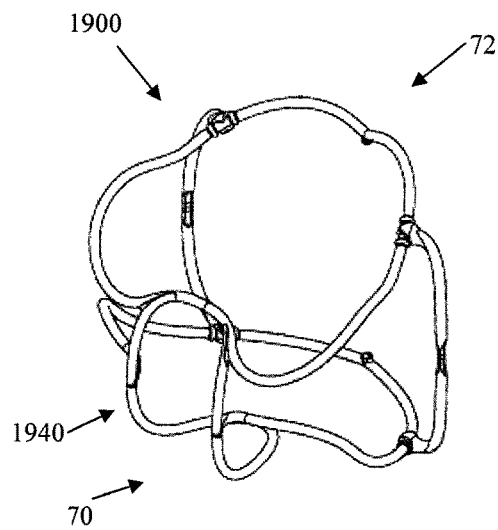
FIGS. 19A-19D illustrates an alternative embodiment of a foldable frame without a tongue cover.
Figure 19B:
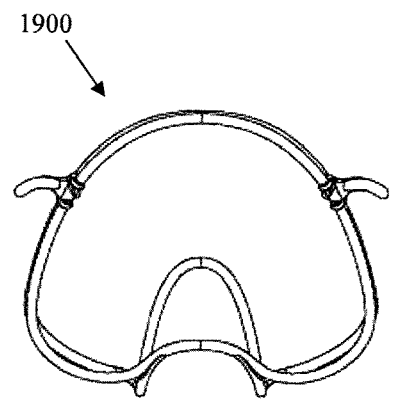
Figure 19C:
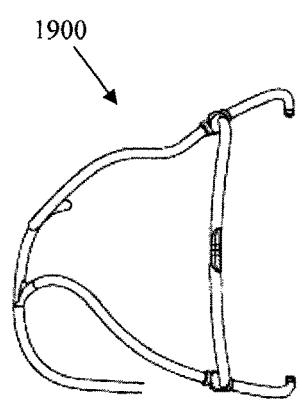
Figure 19D:
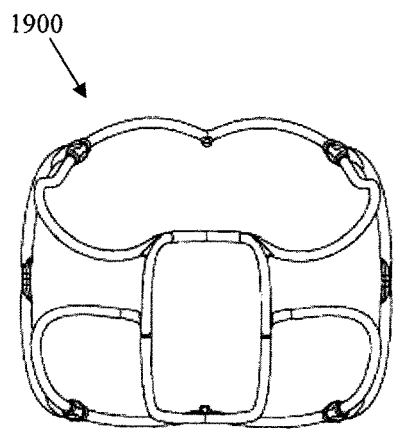

FIGS. 15A-15D illustrate the frame shown in FIGS. 14A-14D together with an evacuation component. The device 1500 has an anterior end 72 and a posterior end 70. FIG. 15A illustrates the frame 1502 comprising a lip ring 1508, and upper frame 1504 having a first end 1505 and a second end 1505' and a lower frame 1506 having a first end 1507 and a second end 1507', wherein respective first ends 1505, 1507 and second ends 1505', 1507' are connected via a cross-member 1540, wherein the lower frame has evacuation inlets 1512. FIG. 15B illustrates a top view of the upper and lower frame, 1504, 1506, respectively, the lip ring 1508, and inlets 1512 in the bottom frame 1506. FIG. 15C is a side view of the frame 1502 of the device 1500 including upper and lower frames 1504, 1506, lip ring 1508, and inlets located in the lower frame 1506. FIG. 15D is a posterior view of the retraction device 1500 including upper and lower frame 1504, 1506, lip ring 1508, and inlets 1512 from the evacuation component of the device.

FIGS. 16A-16D are views of an isolated lip ring. FIG. 16A is a perspective view of the lip ring 1608 from the posterior side of the lip ring. The lip ring can have attachment fittings 1609 for attaching the lip ring 1608 to the frame of the retraction device. FIG. 16B is a top view of the lip ring 1608. FIG. 16C is a side view of the lip ring 1608; FIG. 16D is a posterior view of the lip ring 1608.

FIGS. 17A-17 are isolated views of a tongue retractor. The tongue retractor can be a wire structure. Alternatively, the tongue retractor can comprise a structure that extends into a volume of space forward from the wire structure. The tongue can occupy the space underneath the tongue retractor cover. The tongue retractor can serve to contain and confine the tongue in a restricted space, thereby preventing the tongue from filling the oral cavity. FIG. 17A is a perspective view of a tongue retractor 1710. The tongue retractor 1710 can be a simple structure consisting of a wire frame. Alternatively, the tongue retractor 1710 can comprise a cover 1711 for encasing the tongue retractor 1710. The tongue retractor can contain the tongue from at least one side of the tongue. Alternatively, the tongue retractor can contain the tongue from both sides of the tongue. In some embodiments, the tongue retractor can confine the tongue in its entirety. The tongue retractor can confine the tongue to a restricted space, thereby preventing the tongue from filling the oral cavity. FIG. 17B is a top view of the tongue retractor 1710. FIG. 17C is a side view of a tongue retractor 1710. FIG. 17D is a posterior view of the tongue retractor 1710.

In some embodiments, the retraction device can be of the embodiments shown in FIGS. 18A-18D. The retraction device 1800 has an anterior end 72 and a posterior end 70 and can further comprise a hinge 1828 that can be used to further alter the shape of the retraction device 1800. In some embodiments, the hinge can be a flexible material hinge. As shown in FIG. 18A, the retraction device 1800 can comprise an upper frame 1804 having a first end 1805 and a second end 1805', a lower frame 1806 having a first end 1807 and a second end 1807' wherein the respective first ends 1805, 1807 and second ends 1805', 1807' are connected via a cross-member 1840, and a tongue retractor 1810 having an elongated structure with an upper end and a lower end when viewed from a sagittal plane perspective, a curved shape when viewed from a coronal plane perspective, and a surface between said upper and lower ends to limit forward movement of a tongue toward a patient's teeth. The upper and lower frames 1804, 1806, respectively can be in mechanical communication through at least one support 1830. The support can comprise a hinge 1828 for collapsing the upper frame 1804 toward the lower frame 1806. The hinge 1828 can facilitate the compression of the device 1800 to undertake a more compact structure for ease in inserting into the oral cavity. In some embodiments, the hinge can be located in the side supports. In some embodiments, a hinge can be located in the upper frame 1804 or the lower frame 1806 or both the upper and lower frames 1804, 1806. The support can be rigidly affixed to the upper and lower frames. Alternatively, the support 1830 can be a swiveling support 1830 as shown in FIG. 18A. FIG. 18B is a top view of the retraction device 1800, illustrating the top frame 1804, the bottom frame 1806, the tongue retractor 1810, and the side supports 1830. FIG. 18C is a side view of a retraction device 1800, illustrating the top frame 1804, the bottom frame 1806, tongue retractor 1810, side support 1830, and hinge 1828. FIG. 18D is a posterior view of the retraction device 1800.

FIGS. 19A-19D show an embodiment of the retraction device 1900 having an anterior end 72, a posterior end 70, a cross member 1940, and a hinge and swivel supports but without a tongue retractor.

Isolated supports 2030, 2030' are shown in FIGS. 20A-20D. In some embodiments, the supports 2030, 2030' have at least one hinge 2028, 2028'. In some embodiments, the supports comprise multiple hinges. FIG. 20A is a perspective view of the isolated supports 2030, 2030'. FIG. 20B is a top view of the isolated supports 2030, 2030'. FIG. 20C is a side view of one of the supports 2030 with a hinge 2028. FIG. 20D is a posterior view of two isolated supports 2030, 2030' and their respective hinges 2028, 2028'.

FIGS. 21A-21D illustrate a lower arch retraction device 2100 having an anterior end 72, a posterior end 70, a lip ring 2108 with light ring 2114, and a tongue retractor 2110 having an elongated structure with an upper end and a lower end when viewed from a sagittal plane perspective, a curved shape when viewed from a coronal plane perspective, and a surface between said upper and lower ends to limit forward movement of a tongue toward a patient's teeth. The tongue retractor is braced between the upper palate and below the tongue area. The lip ring connects to the bottom of the frame. When present, an evacuation component is then positioned over the top of the lip ring to form a single unit. The lip ring 2118 is held in place by the upper lip in conjunction with the lip rest 2118 and the lower soft tissue anatomy surrounding the area. The device can have a frame covered with a soft membrane cover as shown in FIG. 21A. In some embodiments, suction can be administered to the oral cavity through inlets 2112 in the soft membrane. FIG. 21B is a top view of the retraction device 2100, illustrating the lower frame 2106 having a first end 2107 and a second end 2107', wherein first end 2107 and second end 2107' are connected via a cross member 2140, with lower gum protection cover 2122, inlets in the lower frame 2106 and lower gum protection cover 2122, and lip ring 2108 with light ring 2114 and light sources 2116, 2116'. FIG. 21C is a side view of the retraction device 2100. FIG. 21D is a posterior view of the retraction device 2100.

Figure 22A:
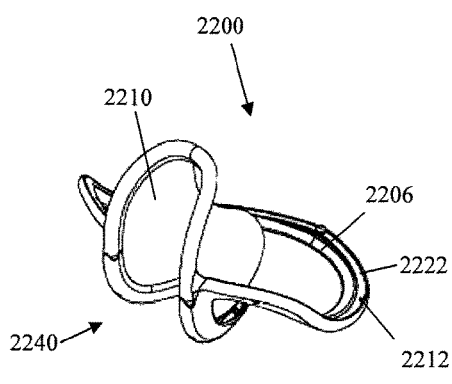
FIGS. 22A-22D illustrates an alternative embodiment of a retraction device comprising a frame with gum protector and tongue cover.
Figure 22B:
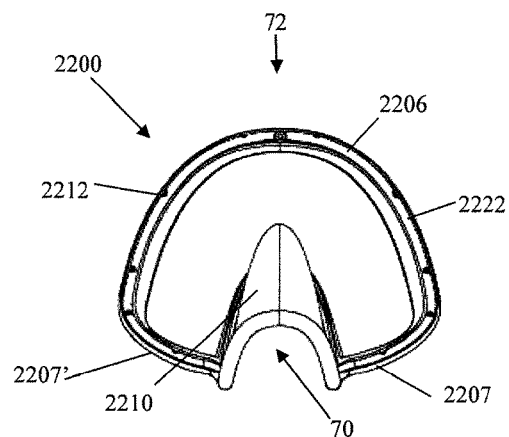
Figure 22C:
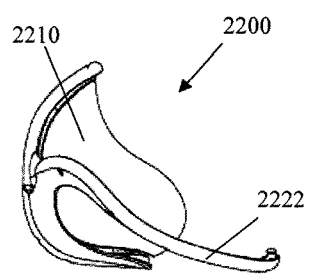
Figure 22D:
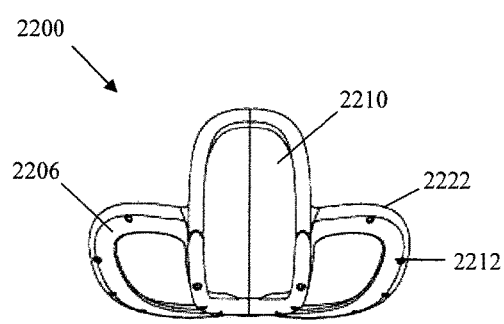

FIGS. 22A-22D illustrate an alternative embodiment of a retraction device 2200 having an anterior end 72 and a posterior end 70 and comprising a frame 2206 with gum protector 2222 without a lip ring. FIG. 22A is a perspective view of a retraction device 2200. FIG. 22B is a top view of a retraction device 2200 illustrating a lower frame 2206 having a first end 2207 and a second end 2207' wherein first end 2207 and second end 2207' are connected via a cross-member 2240, with gum protector 2222 with inlets 2212 along the lower frame 2206, and tongue retractor 2210 having an elongated structure with an upper end and a lower end when viewed from a sagittal plane perspective, a curved shape when viewed from a coronal plane perspective, and a surface between said upper and lower ends to limit forward movement of a tongue toward a patient's teeth. FIG. 22C is a side view of the retraction device 2200. FIG. 22D is a posterior view of the retraction device 2200.

Figure 23A:
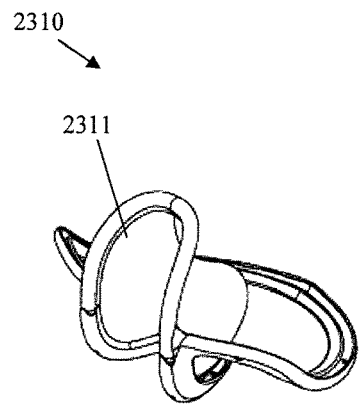
FIGS. 23A-23D illustrate an alternative embodiment of a membrane isolated from the retraction device comprising a gum protector, a tongue cover and evacuation component.
Figure 23B:
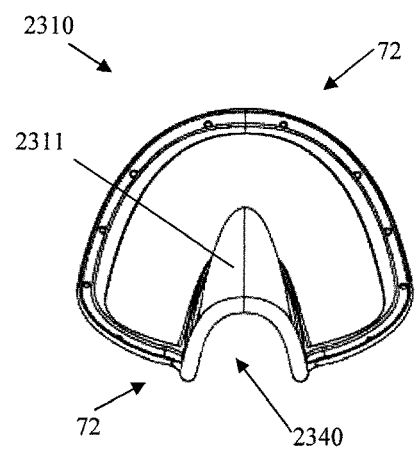
Figure 23C:
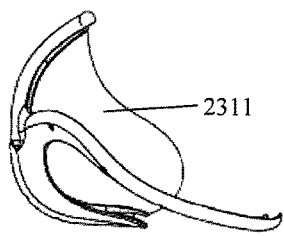
Figure 23D:
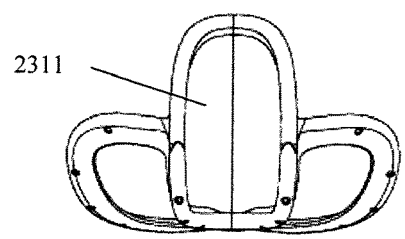

FIGS. 23A-23D illustrate a tongue retractor membrane or cover 2311 configuration. The device has an anterior end 72, a posterior end 70, and at least one cross-member 2340. FIG. 23A illustrates a perspective view of the tongue retractor 2310 as viewed from the posterior side of the device. FIG. 23B illustrates a top view of the tongue retractor 2311 with cover 2311. FIG. 23C illustrates a side view of the tongue retractor 2310 having an elongated structure with an upper end and a lower end when viewed from a sagittal plane perspective, a curved shape when viewed from a coronal plane perspective, and a surface between said upper and lower ends to limit forward movement of a tongue toward a patient's teeth. FIG. 23D is a posterior view of the tongue retractor cover 2310.

FIGS. 24A-24D illustrate a view of an isolated lower frame 2406 from a lower arch retraction device. The device has an anterior end 72, a posterior end 70, and at least one cross-member 2440. In some embodiments, the lower frame comprises at least one inlet 2412 for evacuating the oral cavity. FIG. 24A illustrates a perspective view of the frame 2406. FIG. 24B is a top view of the lower frame 2406 having a first end 2407 and a second end 2407'. FIG. 24C is a side view of the frame 2406. FIG. 24D is a posterior view of the frame 2406.

Figure 25A:
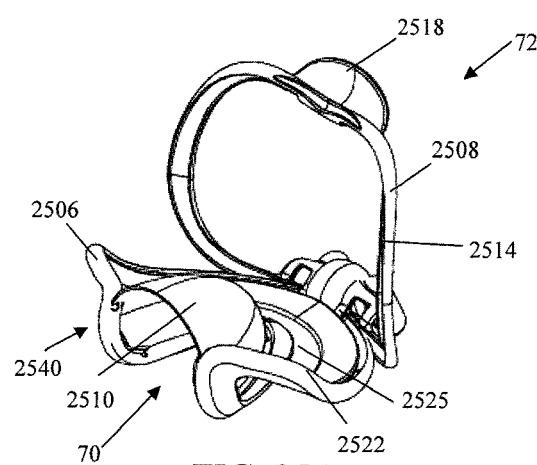
FIGS. 25A-25D illustrate an alternate embodiment of a retraction device comprising a lower frame and gum protector and light lip ring.
Figure 25B:
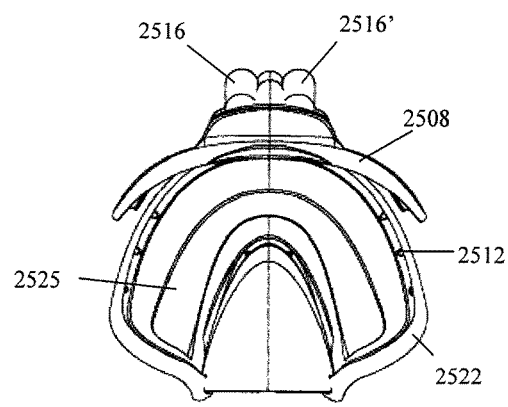
Figure 25C:
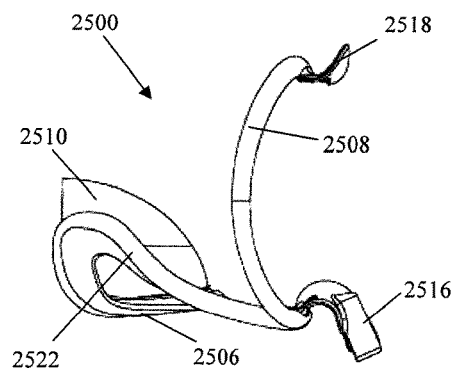
Figure 25D:
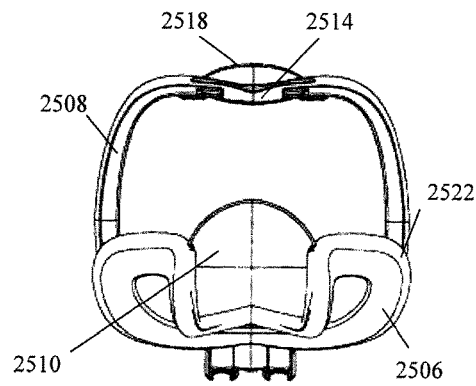

FIGS. 25A-25D illustrate an alternative embodiment of a lower frame retraction device 2500. The device shown in FIGS. 25A-25D illustrate a device that has leverage once positioned in the mouth to hole the bottom arch in position, thereby preventing the tongue from lifting the bottom arch out of position. The device has an anterior end 72, a posterior end 70, and at least one cross-member 2540. FIG. 25A is a perspective view of the lower frame retraction device 2500. The retraction device 2500 shown in FIG. 25A does not rely upon the upper palette and the tongue retractor 2510 to stabilize the device 2500. Therefore, the device is less intrusive than other devices and can further facilitate scanning the oral cavity. FIG. 25A also illustrates a device 2500 having a lower frame 2506 with gum protection cover 2522 with an opening 2525 for the dental arch. The device can also have a lip ring 2508 with a light ring 2514 having lights 2516, 2516' thereon and lip rest 2518. FIG. 25B illustrates a top view of the device 2500. FIG. 25C illustrates a side view of the device 2500. FIG. 25D illustrates a posterior view of the device 2500.

Figure 26A:
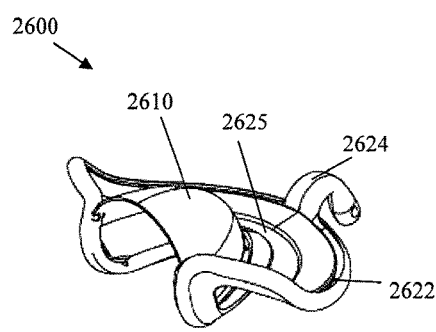
FIGS. 26A-26D illustrate an alternate embodiment of a retraction device comprising a lower arch frame and a tongue cover.
Figure 26B:
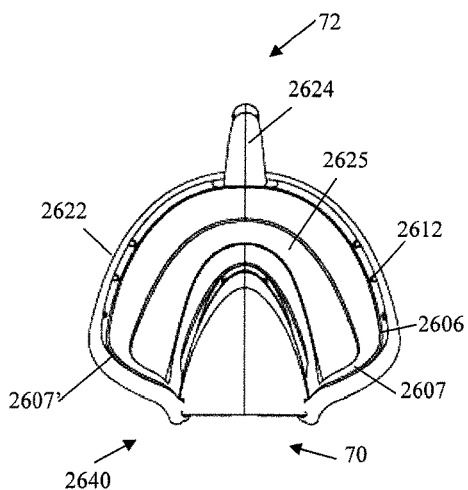
Figure 26C:
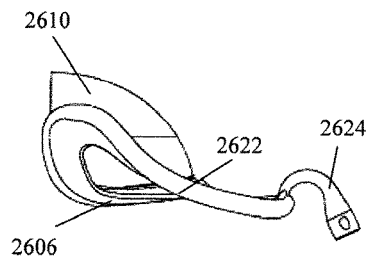
Figure 26D:
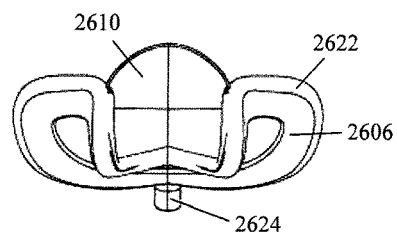

An alternate embodiment of a lower arch retraction device 2600 is shown in FIGS. 26A-26D. The device has an anterior end 72, a posterior end 70, and at least one cross-member 2640. FIG. 26A illustrates a lower frame 2606, having a first end 2607 and a second end 2607', with a gum cover 2622, and a tongue retractor 2610. An opening 2625 for the dental arch is shown in FIG. 26A. Furthermore, a suction port 2624 can connect the retraction device 2600 to a source of suction to evacuate the oral cavity through at least one inlet 2612 located in the frame or gum protector or both. FIG. 26B is a top view of the retraction device showing the suction port 2624 and inlets 2612 in communication, preferably fluid communication, with the suction port 2624, the lower frame 2606 and gum protection cover 2622, tongue retractor 2610, and the opening 2625 for the dental arch in the retraction device 2600. FIG. 26C is a side view of a retraction device 2600 illustrating the frame 2606, the gum protection cover 2622, the tongue retractor 2610, and suction port 2624. FIG. 26D is a posterior view of the retraction device 2600.

Figure 27A:
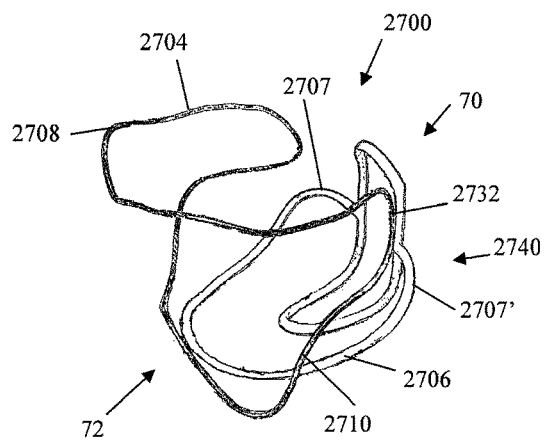
FIGS. 27A-27D illustrates an alternative embodiment of retraction device comprising an upper and lower arch frame and tongue cover.
Figure 27B:
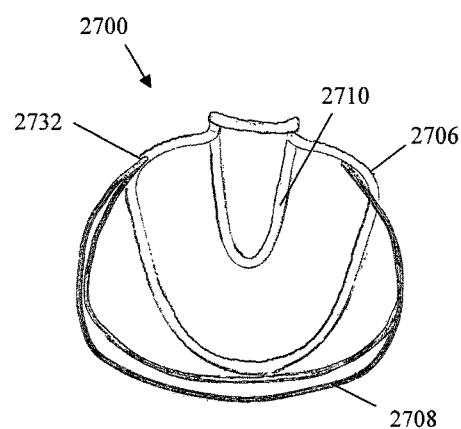
Figure 27C:
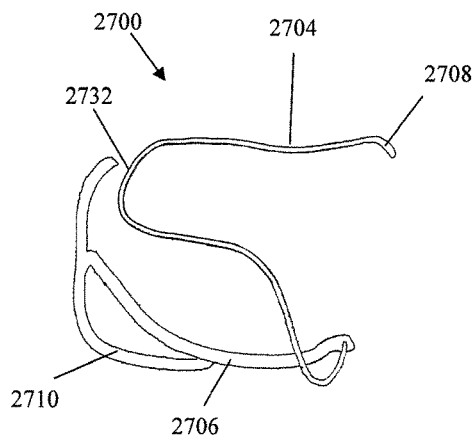
Figure 27D:
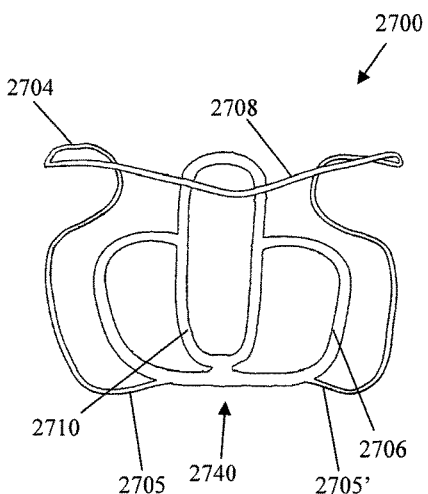

FIGS. 27A-27D illustrate an alternate embodiment of an isolated lower arch retraction device 2700. The device has an anterior end 72 and a posterior end 70. FIG. 27A illustrates a retraction device 2700 comprising an alternate embodiment of a lip ring 2708, an upper frame 2704 having a first end 2705 and a second end 2705', a lower frame 2706 having a first end 2707 and a second end 2707' wherein respective first ends 2705, 2707 and second ends 2705', 2707' are connected via a cross-member 2740, and a tongue retractor 2710 having an elongated structure with an upper end and a lower end when viewed from a sagittal plane perspective, a curved shape when viewed from a coronal plane perspective, and a surface between said upper and lower ends to limit forward movement of a tongue toward a patient's teeth. The retraction device 2700 also has a posterior balancing positional support 2732 which aids in the insertion of the device into the oral cavity and provides posterior balancing positional support. The posterior balancing positional supports 2732 contact the back of the cheeks to balance forces from the front of the cheeks in order to properly center the device along the posterior/anterior axis. FIG. 27B is a top view of the retraction device 2700 illustrating the lip ring, 2708, lower frame 2706, tongue retractor 2710, and posterior supports 2732. FIG. 27C is a side view of the retraction device, showing the lip ring 2708, lower frame 2706, tongue retractor 2710, and posterior supports 2732. FIG. 27D is a frontal view of the retraction device 2700 illustrating the lip ring 2708, lower arch frame 2706, tongue retractor 2710, and posterior supports 2732.

Figure 28A:
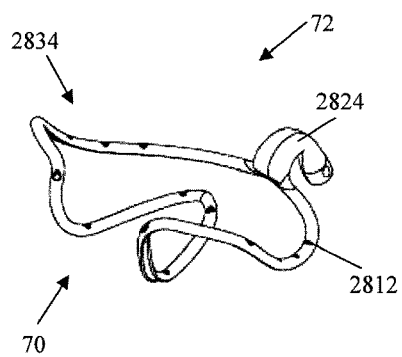
FIGS. 28A-28D illustrate an alternate embodiment of an isolated frame comprising a evacuation component.
Figure 28B:
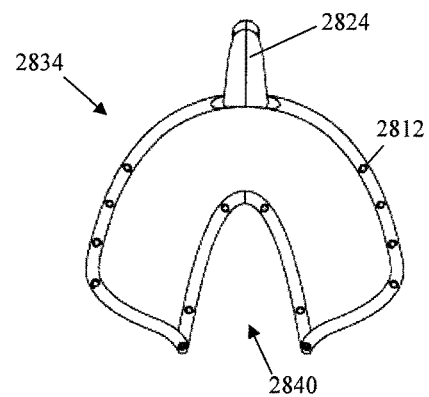
Figure 28C:
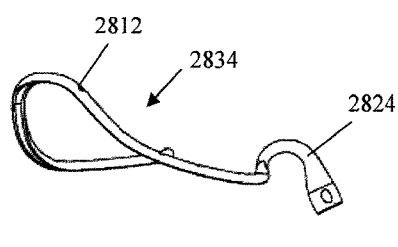
Figure 28D:
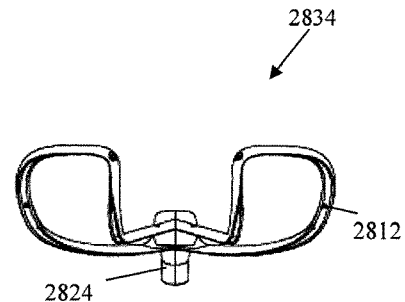

FIGS. 28A-28D illustrate an isolated evacuation element 2834. The device has an anterior end 72, a posterior end 70, and at least one cross-member 2840. FIG. 28A is a perspective view of an evacuation element 2834 as viewed from the posterior side. The evacuation element can be in communication with a suction source through the suction port 2824. The evacuation element 2834 can be used to evacuate the oral cavity through at least one inlet 2812 located in the evacuation element 2834. In some embodiments, multiple evacuation elements 2812 can be located along the length of the evacuation element, as shown in FIG. 28A. In some embodiments, inlets 2812 can be located along the interior of the cheeks. In some embodiments, inlets 2812 can be located around the tongue. Inlets 2812 can be located along both the cheeks and the tongue. FIG. 28B is a top view of the evacuation element. FIG. 28C is a side view of the evacuation element 2834. FIG. 28D is a posterior view of the evacuation element 2834.

Figure 29A:
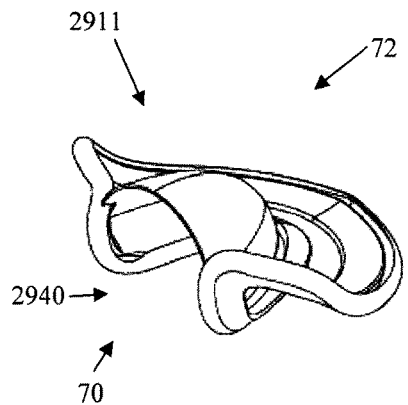
FIGS. 29A-29D illustrate an isolated tongue cover.
Figure 29B:
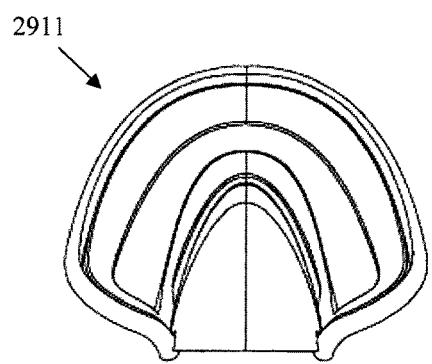
Figure 29C:
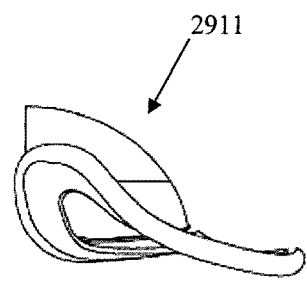
Figure 29D:
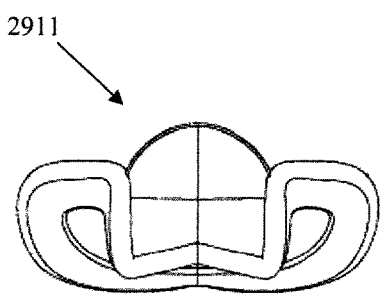

FIGS. 29A-29D illustrate an isolated tongue deflection cover 2911. The device has an anterior end 72, a posterior end 70, and at least one cross-member 2940. The tongue deflection cover can be used to deflect the tongue out of the working space to facilitate scanning the dental surfaces. FIG. 29A illustrates a perspective view of the tongue deflection cover 2911 as viewed from the posterior side. FIG. 29B illustrates a top view of the tongue deflection cover 2911. FIG. 29C illustrates a side view of a tongue deflection cover. FIG. 29D illustrates a posterior view of the tongue deflection cover.

Figure 30A:
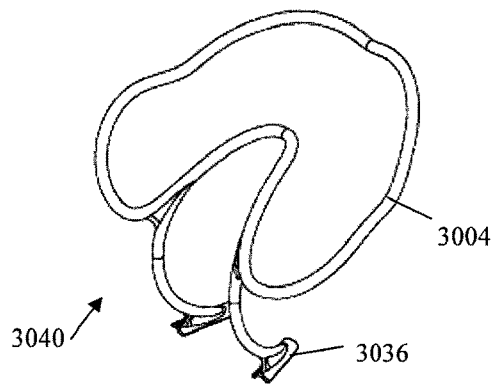
FIGS. 30A-30D illustrates an isolated upper arch frame.
Figure 30B:
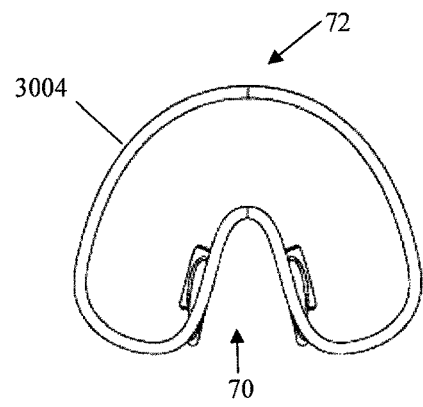
Figure 30C:
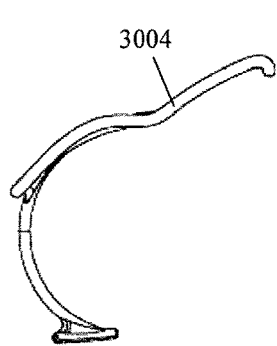
Figure 30D:
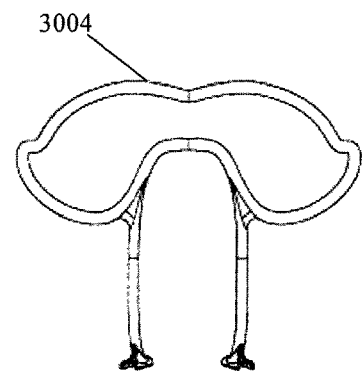

FIGS. 30A-30D illustrate an isolated upper arch frame 3004. The device has an anterior end 72, a posterior end 70, and at least one cross-member 3040. The upper arch frame 3004 can be used in conjunction with a lower arch retraction device. The upper arch frame 3004 can be used to provide optional support for upper retraction of the soft tissue in the oral cavity. FIG. 30A illustrates one embodiment of an upper arch frame 3004. The arch support can comprise connectors 3036 to connect the upper arch frame 3004 to the retraction device. The upper arch frame 3004 can be connected to the lower retraction device by snapping the upper arch frame 3004 and the lower retraction device together. Alternatively, the upper arch frame 3004 can connected to the lower retraction device by screwing the pieces together. Alternatively, the upper arch frame can be adhered to the lower retraction device by any suitable adhesive or mechanism for adhering the two units together including but not limited to, glue, tape, rubber bands, or any combination thereof. FIG. 30B is a top view of an isolated upper arch frame 3004. FIG. 30C is a side view of an upper arch frame. FIG. 30D is a posterior view of an upper arch frame.

Figure 31A:
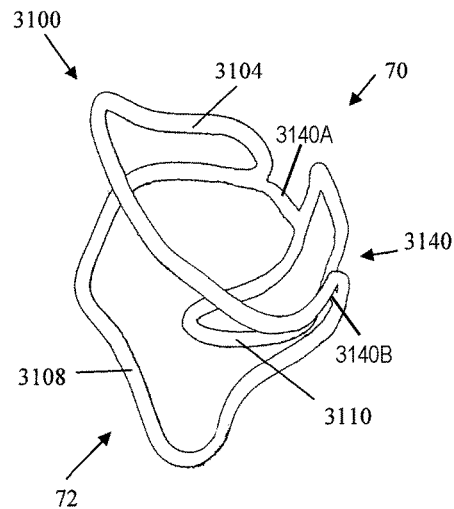
FIGS. 31A-31D illustrates an alternative embodiment of an isolated upper and lower arch frame.
Figure 31B:
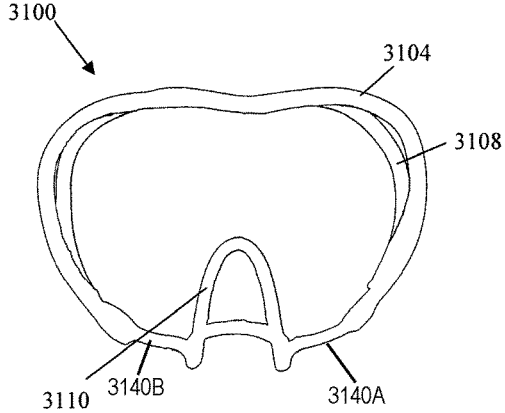
Figure 31C:
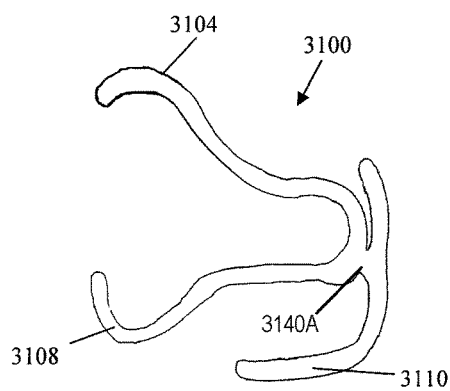
Figure 31D:
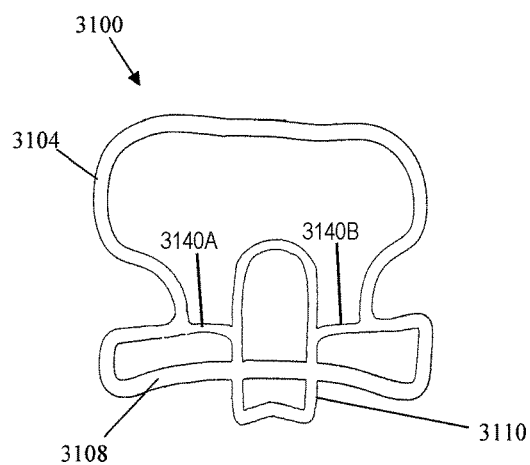

FIGS. 31A-31D illustrate an alternative embodiments of an isolated upper arch retraction device 3100 including a lower arch frame 3108. The device has an anterior end 72, a posterior end 70, and at least one cross-member 3140, which includes a first lateral extension 3140A and a second lateral extension 3140B. In some embodiments, the retraction device is a single piece. In some embodiments, the retraction device 3100 can be more than one piece, where the pieces are assembled prior to inserting the device into the oral cavity. The lip ring can be attached to the frame at the posterior end of the device 3100. FIG. 31A is a perspective view of upper arch retraction device 3100 having the lower arch frame 3108, an upper arch frame 3104, and a tongue retractor 3110 attached to the first and the second lateral extensions 3140A and 3140B and having an elongated structure with an upper end and a lower end when viewed from a sagital plane perspective, a curved shape when viewed from a coronal plane perspective, and a surface between said upper and lower ends to limit forward movement of a tongue toward a patient's teeth. In some embodiments, the device 3100 further comprises a tongue cover for containing the tongue. FIG. 31B is a top view of the retraction device 3100, illustrating the upper arch frame 3104, the lower arch frame 3108, the first and second lateral extensions 3140A and 3140B, and tongue retractor 3110. FIG. 31C is a side view of the retraction device 3100. FIG. 31D is a frontal view of the retraction device 3100.

Figure 32A:
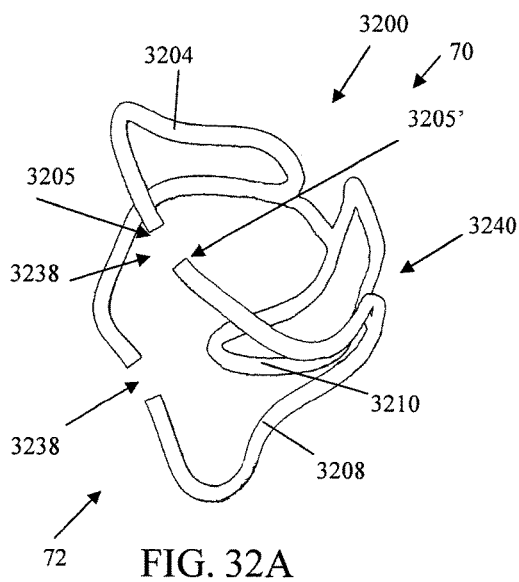
FIGS. 32A-32D illustrates an alternative embodiment of a retraction device frame.
Figure 32B:
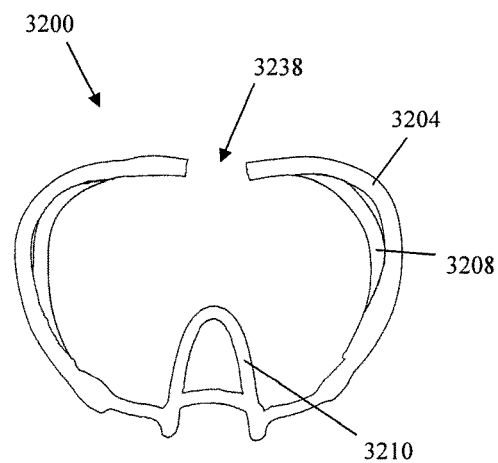
Figure 32C:
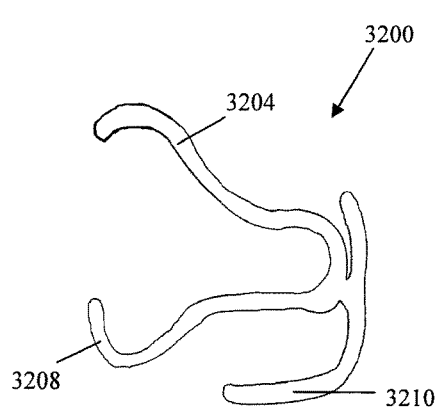
Figure 32D:
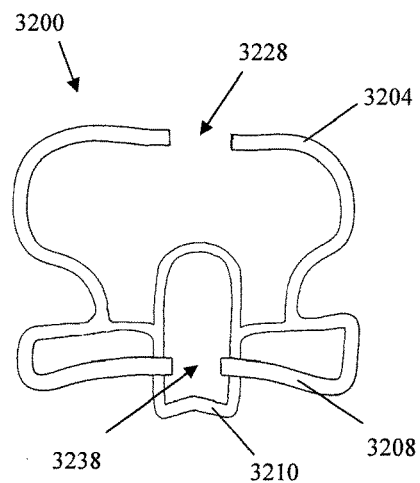

FIGS. 32A-32D illustrate an alternative embodiment of a retraction device 3200. The device has an anterior end 72, a posterior end 70, and at least one cross-member 3240. In this embodiment, the upper retraction frame 3204 has a first end 3205 and a second end 3205' and is separated by a gap 3238. In some embodiments, the lower arch frame 3208 can have a gap 3238. In some embodiments, both the upper frame 3204 and the lower arch frame 3208 have a nap 3238, as shown in FIG. 32A. The device can have a tongue retractor 3210 having an elongated structure with an upper end and a lower end when viewed from a sagital plane perspective, a curved shape when viewed from a coronal plane perspective, and a surface between said upper and lower ends to limit forward movement of a tongue toward a patient's teeth. FIG. 32B is a top view of a retraction device 3200 with a gap 3238. FIG. 32C illustrates a side view of a retraction device 3200. FIG. 32D illustrates a front view of the retraction device 3200.

II. Methods

Further provided herein are methods of use of the invention described herein. Provided herein is a method of retracting tissue in an oral cavity comprising: inserting a retraction device comprising a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity; and positioning the retraction device in the oral cavity to create an isolated working field. The positioning step can be performed in less than 1 minute. In some embodiments, the positioning step can be performed in less than 20 seconds.

Yet another method for retracting tissue in an oral cavity comprises: inserting a retraction device comprising a topology conformable structure adaptable to create a working field in an oral cavity of a patient, wherein the working field is at least 10% larger than a working field in oral cavity of the patient without use of the device; and positioning the retraction device in the oral cavity to create an isolated working field.

Another method provided herein is a method of facilitating the creation of an oral cavity model comprising: inserting a retraction device comprising a topology conformable structure adaptable to be in a constrained shape that can be delivered into an oral cavity and further adaptable to be in an unconstrained shape to create a useable working field in the oral cavity, the usable working field providing increased accessibility to and increased visibility within the oral cavity; and positioning the retraction device in the oral cavity to create the useable working field in the oral cavity. In some embodiments, the method can further comprise the step of illuminating the oral cavity with the retraction device. Additionally, the method can comprise the step of applying a powder to the at least one dry tooth surface.

III. Materials of Manufacture

As will be appreciated by those skilled in the art, the devices described herein, and other device designs that can be employed under the invention based on the teachings herein, and their components can be made from a variety of materials known in the art. Candidate materials for the devices and components would be known by persons skilled in the art and include, for example, the materials described above as well as suitable biocompatible materials such as metals (e.g. stainless steel, shape memory alloys, such a nickel titanium alloy nitinol) and engineering plastics (e.g. polycarbonate). See, for example U.S. Pat. No. 5,190,546 to Jervis for Medical Devices Incorporating SIM Memory Alloy Elements and U.S. Pat. No. 5,964,770 to Flomenblit for High Strength Medical Devices of Shape Memory Alloy. For example, a device frame may be made of materials such as titanium, cobalt chrome stainless steel. Alternatively, a sheath or outer layer covering a frame can be made of biocompatible polymers such as polyetheretherketone (PEEK), polyarylamide, polyethylene, and polysulphone. See, for example U.S. Pat. No. 5,190,546 to Jervis for Medical Devices Incorporating SIM Memory Alloy Elements and U.S. Pat. No. 5,964,770 to Flomenblit for High Strength Medical Devices of Shape Memory Alloy. Other materials may be appropriate for some or all of the components, such as biocompatible polymers, including polyetheretherketone (PEEK), polyarylamide, polyethylene, and polysulphone. U.S. Pat. No. 5,964,770 to Flomenblit for High Strength Medical Devices of Shape Memory Alloy.

A variety of hydrophillic materials, hydrophobic materials, or putties can also be used, e.g. to form seals. Such materials would be known to a person skilled in the art and include, for example, hydrophilic material or a putty (e.g., Van-R reversible hydrocolloid, available from Dux Dental, and vinyl polysiloxane, available from 3M Express), as discussed above. Other materials that might also be used include, for example, poly(vinyl alcohol) (PVA) hydrogels, hydrophillic, medical grade foam, polysaccharides, glucosaminoglycans. Additional materials can include, silicons, thermal plastic elastiomers (TPE), thermal plastic urethanes (TPU), nylons and material, epoxies, corn polymers or other environmentally friendly materials, or any combination thereof. The material can also be any suitable biocompatible material.

In some embodiments, the device can be constructed from materials having different properties. In some embodiments, the devices described herein can be created from single property membrane transformed into multiple properties. The material can harden through additional processes, such as by changing the molecular structure of the material. In some embodiments, the material can be placed over a frame or device. The material can then undergo a process that can change the material properties of the material. In some embodiments the material property of the device is the same throughout. Alternatively, the device can be comprised of material having different properties. For example, the material of the device can be harder or stiffer in some areas and softer in other areas. The properties of the material can be changed using a laser. Alternatively, the properties of the material can be changed using light. The properties of the material can be changed using any suitable method for altering the material characteristics of the material including, but not limited to, temperature and pH, laser curing, stereolithographic laser polymerization and crosslinking, optical post manufacturing processing, and chemical post manufacturing processing, or any combination thereof.

IV. Kits

The invention also contemplates a kit comprising one or more devices with one or more device products associated with a particular dental treatment. For example, lasers are currently used in dentistry for various applications including but not limited to: cavity removal, cutting or hardening bonding material, whitening teeth, and re-contouring, reshaping, or removing gum tissue. The device herein can be used in combination with laser therapy to act as a shield and tongue and cheek retractor, preventing other regions of the mouth from being affected by the laser. Thus compounds used with the laser procedure could be provided in the kit with the devices or devices, as well as equipment adaptors, etc.

Additionally, a kit comprising one or more devices with one or more complementary automatic impression tray system(s) or implant specific impression tray(s), which are designed to fit over the upper and/or lower arches of teeth, to capture a detailed and accurate impression of each full arch of teeth and the surrounding alveolar process and gingiva, which the device is in place. This prevents any contamination of the impression(s) with saliva and prevents any escape of impression materials into the mouth cavity or the patient's throat.

Further provided herein are kits for retracting tissue in an oral cavity. Provided herein are kits for retracting tissue in an oral cavity comprising: a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity. In some embodiments, the kit can further comprise a tongue retractor. Additionally, the kit can further comprise a light ring. Furthermore, the kit can comprise an evacuation component. The kit can further comprise a membrane adaptable to be fitted over the frame. In some embodiments, the kit can further comprise a gum protection cover. The kit can also further comprise a lip ring.

Furthermore, additionally provided herein is a kit for retracting tissue in an oral cavity comprising: a retraction device comprising a topology conformable structure adaptable to be in a constrained shape that can be delivered into an oral cavity and further adaptable to be in an unconstrained shape to create a useable working field in the oral cavity, the useable working field providing increased accessibility to and increased visibility within the oral cavity; and a kit of secondary dental products wherein tissue retraction in the oral cavity is necessary. In some embodiments, the kit can further comprise an illumination source. Additionally, the kit can comprise at least one optical scanner or digital scanner. Furthermore, the kit can further comprise a powder for facilitate scanning of the dental surfaces. In some embodiments, the kit can further comprise a whitening or bleaching kit.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A soft tissue retraction device, comprising:
a flexible frame selectively collapsible to facilitate insertion into a mouth of a patient and expandable, the flexible frame comprising:
an upper frame element positionable around an outer surface of an upper dental arch of the mouth and extending between an upper anterior end and a right posterior end and a left posterior end;
a lower frame element that is interconnected with the upper frame element at the right posterior end and the left posterior end, the lower frame element being positionable around an outer surface of a lower dental arch of the mouth and extending between a lower anterior end and the right and left posterior ends;
a first lateral extension interconnected with the lower frame element and the upper frame element at the left posterior end;
a second lateral extension interconnected with the lower frame element and the upper frame element at the right posterior end; and
a tongue retractor attached to the first and the second lateral extensions,
wherein:
each of the first and second lateral extensions is posteriorly curved between the left and right posterior ends and the tongue retractor such that the left and right posterior ends are anterior to at least a portion of the first and the second lateral extensions;
each of the first and second lateral extensions are configured to extend posteriorly behind posterior teeth in the mouth and configured to permit engagement of occlusal tooth surfaces of the posterior teeth; and
the flexible frame is sized and configured to reside substantially entirely within the mouth when the frame is in an expanded configuration.

2. The soft tissue retraction device of claim 1, wherein:
the first and second lateral extensions are included in a flexible bridge; and
the flexible bridge connects the posterior ends of the upper and lower frame elements.

3. The soft tissue retraction device of claim 1, wherein the tongue retractor is configured to at least partially cover a tongue of the patient to confine the tongue in a restricted space in a posterior region of the mouth and limit a movement of the tongue.

4. The soft tissue retraction device of claim 3, wherein the tongue retractor comprises a flexible membrane and is adaptable to compress at least a portion of the tongue.

5. The soft tissue retraction device of claim 1, further comprising a lip rest comprising a flange curving upward from the upper anterior end of the upper frame element and configured to engage a lip of the patient.

6. The soft tissue retraction device of claim 1, further comprising a lip ring coupled to the upper anterior end and the lower anterior end, the lip ring being configured to bear against and retract a lip of the patient from anterior teeth.

7. The soft tissue retraction device of claim 1, further comprising a flexible membrane attached to the frame, wherein the flexible membrane is configured to reside substantially entirely within an oral cavity when the frame is in an expanded configuration.

8. The soft tissue retraction device of claim 1, further comprising a light source, wherein the light source is attached to the flexible frame or the light source comprises a portion of the flexible frame.

9. The soft tissue retraction device of claim 1, further comprising a gum protector, wherein the gum protector is attached to the flexible frame or the gum protector comprises a portion of the flexible frame.

10. The soft tissue retraction device of claim 1, wherein the flexible frame is formed of a plastic material.

11. The soft tissue retraction device of claim 1, wherein:
the right posterior end and the left posterior end are configured to be positioned posterior to the patient's most posteriorly positioned teeth when the frame is in a mouth; and
a shape of the upper and the lower frame elements generally coincide with an arch shape.

12. A soft tissue retraction device, comprising:
a first frame extending between a first anterior end and a posterior end having a right posterior end and a left posterior end;
a second frame extending between a second anterior end and the posterior end, the second frame being interconnected to the first frame at the right posterior end and at the left posterior end;
a first lateral extension interconnected with the first and second frame at the left posterior end;
a second lateral extension interconnected with the first and second frame at the right posterior end; and
a tongue retractor attached to the first and the second lateral extensions and configured to at least partially cover a tongue of a patient to limit a movement of the tongue,
wherein:
the first and second frames form a flexible frame adaptable between a constrained shape in which the first and second anterior ends of the first and second frames are compressed together and an unconstrained shape in which the first and second anterior ends of the first and second frames come apart;
the first lateral extension is posteriorly curved between the left posterior end and the tongue retractor such that the left posterior end is anterior to first lateral extension;
the second lateral extension is posteriorly curved between the right posterior end and the tongue retractor such that the right posterior end is anterior to the second lateral extension; and
the right posterior end and the left posterior end are configured to be positioned posterior to the patient's most posteriorly positioned teeth when the frame is in a mouth.

13. The soft tissue retraction device of claim 12, wherein at least one of the first and second frames comprises a curved region adjacent to the posterior end.

14. The soft tissue retraction device of claim 12, wherein the shape of the first and second frames generally coincide with an arch shape.

15. The soft tissue retraction device of claim 12, wherein:
the first anterior end of the first frame is configured to extend or protrude an upper lip away from teeth of an upper dental arch; and
the second anterior end of the second frame is configured to extend or protrude a lower lip away from teeth of a lower dental arch when the frame is in the unconstrained shape.

16. The soft tissue retraction device of claim 12, further comprising a lip ring coupled to the first anterior end and the second anterior end, the lip ring being configured to bear against and retract a lip of the patient from anterior teeth.

17. The soft tissue retraction device of claim 12, further comprising a light source, wherein the light source is attached to the first frame, the light source is attached to the second frame, the light source comprises a portion of the first frame or the light source comprises a portion of the second frame.

18. The soft tissue retraction device of claim 12, wherein the flexible frame is sized and configured to reside substantially entirely within the mouth when the flexible frame is in an unconstrained shape.

19. A soft tissue retraction device, comprising:
a flexible frame selectively collapsible to facilitate insertion into a mouth and expandable to retract soft tissue when inserted in the mouth, the frame comprising:
an upper frame element positionable around an outer surface of an upper dental arch and extending between an upper anterior end and a left posterior end and a right posterior end;
a lower frame element positionable around an outer surface of a lower dental arch and extending between a lower anterior end and the left posterior end and the right posterior end;
a first lateral extension connected to the left posterior end;
a second lateral extension connected to the right posterior end; and
a tongue retractor attached to the first and the second lateral extensions, the tongue retractor being configured to at least partially cover a tongue to limit a movement of the tongue,
wherein:
the upper and lower frame elements are interconnected at the left posterior end and the right posterior end that are positionable at the back of the mouth;
each of the first and second lateral extensions are posteriorly curved between the left posterior end and the right posterior end and the tongue retractor such that the left posterior end and the right posterior end are anterior to the first and the second lateral extensions; and
a shape of the upper and the lower frame generally coincide with an arch shape.

20. The soft tissue retraction device of claim 19, wherein the tongue retractor comprises a flexible membrane that extends toward the upper and lower anterior ends such that a space is created that is configured to receive the tongue.

21. The soft tissue retraction device of claim 19, further comprising a lip ring coupled to the upper anterior end and the lower anterior end, the lip ring being configured to bear against and retract a lip of the patient from anterior teeth.

22. The soft tissue retraction device of claim 19, further comprising a light source, wherein the light source is attached to the flexible frame or the light source comprises a portion of the flexible frame.

23. The soft tissue retraction device of claim 19, wherein:
the right posterior end and the left posterior end are configured to be positioned posterior to a patient's most posteriorly positioned teeth when the flexible frame is in a mouth; and
the flexible frame is sized and configured to reside substantially entirely within the mouth when the frame is in an expanded configuration.

* * * * *